US010857258B2

(12) United States Patent
Yoon

(10) Patent No.: US 10,857,258 B2
(45) Date of Patent: *Dec. 8, 2020

(54) ADHESIVE PEPTIDE AND USE THEREFOR

(71) Applicant: Won-Joon Yoon, Seoul (KR)

(72) Inventor: Won-Joon Yoon, Seoul (KR)

(73) Assignee: SEWON BIOTECHNOLOGY INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/714,357

(22) Filed: Sep. 25, 2017

(65) Prior Publication Data

US 2018/0085488 A1 Mar. 29, 2018

Related U.S. Application Data

(63) Continuation-in-part of application No. PCT/KR2016/002864, filed on Mar. 22, 2016.

(30) Foreign Application Priority Data

Mar. 26, 2015 (KR) ........................ 10-2015-0042167

(51) Int. Cl.
| | | |
|---|---|---|
| *A61K 38/16* | (2006.01) | |
| *A61K 38/10* | (2006.01) | |
| *A61K 38/08* | (2019.01) | |
| *A61K 38/04* | (2006.01) | |
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61L 24/10* | (2006.01) | |
| *C07K 7/06* | (2006.01) | |
| *C07K 7/08* | (2006.01) | |
| *C07K 14/00* | (2006.01) | |
| *A61K 49/00* | (2006.01) | |
| *C12N 15/63* | (2006.01) | |
| *G01N 33/58* | (2006.01) | |
| *A61K 47/50* | (2017.01) | |
| *C07K 14/435* | (2006.01) | |
| *A61K 47/62* | (2017.01) | |
| *A61K 38/18* | (2006.01) | |
| *A61L 24/00* | (2006.01) | |
| *C12N 5/00* | (2006.01) | |
| *C12N 5/0735* | (2010.01) | |
| *C12N 5/0793* | (2010.01) | |

(52) U.S. Cl.
CPC .............. *A61L 24/10* (2013.01); *A61K 38/04* (2013.01); *A61K 38/08* (2013.01); *A61K 38/10* (2013.01); *A61K 38/16* (2013.01); *A61K 38/1875* (2013.01); *A61K 47/50* (2017.08); *A61K 47/62* (2017.08); *A61K 49/00* (2013.01); *A61L 24/001* (2013.01); *C07K 7/06* (2013.01); *C07K 7/08* (2013.01); *C07K 14/00* (2013.01); *C07K 14/43586* (2013.01); *C12N 5/0068* (2013.01); *C12N 5/0606* (2013.01); *C12N 5/0619* (2013.01); *C12N 15/63* (2013.01); *G01N 33/58* (2013.01); *A61L 2400/06* (2013.01); *C12N 2533/50* (2013.01); *C12N 2539/00* (2013.01)

(58) Field of Classification Search
None
See application file for complete search history.

(56) References Cited

U.S. PATENT DOCUMENTS

| | | | |
|---|---|---|---|
| 2002/0022588 A1 | 2/2002 | Wilkie et al. | |
| 2008/0287651 A1* | 11/2008 | Hiramatsu | ......... A01K 67/0339 530/324 |
| 2018/0282371 A1* | 10/2018 | Yoon | ........................ C07K 7/00 |

FOREIGN PATENT DOCUMENTS

WO 99/66964 A1 12/1999

OTHER PUBLICATIONS

Adessi et al., Curr. Med. Chem. 9:963-978 (2002) (Year: 2002).*
Betts, et al., "Amino Acid Properties and Consequences of Substitutions," in: Bioinformatics for Geneticists, eds., Barnes, et al., John Wiley & Sons, Ltd., pp. 289-316, (2003) (Year: 2003).*
Russell Lab, "Glutamate," available online at http://www.russelllab.org/aas/Glu.html, 2pages (first available 2010) (Year: 2010).*
UniProt Accession No. Q1KS44, 3 pages (2006) (Year: 2006).*
Oxford Reference, "Conservative substitution," available online at https://www.oxfordreference.com/view/10.1093/oi/authority.20110803095633223, 1 page (2019) (Year: 2019).*
U.S. Appl. No. 16/328,476, filed Feb. 19, Yoon, WJ.*

* cited by examiner

*Primary Examiner* — Thea D'Ambrosio
(74) *Attorney, Agent, or Firm* — Vorys, Sater, Seymour & Pease LLP; Mih Suhn Koh

(57) ABSTRACT

Disclosed are novel peptides with adhesive properties to various materials of biological or non-biological origins.

5 Claims, 25 Drawing Sheets

Specification includes a Sequence Listing.

Conjugation method 2: SS-bond conjugation,

PS, PC, Cellulose, Wood, Stainless, Metal

Injection of A7-1 into articular cartilage

*Articular cartilage; #Bone tissue

Injection of A7-1 into articular cartilage

Red fluorescence: A7-1/Cy3 conjugate

Elastic tissue: skin

Elastic tissue: hair

Adipose tissue

Eyeball

F-Peptide: FITC-labeled peptide
Cold: non-labeled peptide

Reporter system: monitoring GFP positive cells or colonies.

Experimental scheme

B, rhBMP2; CL, Cross-linker;
A7-1/B, cross-linked BMP2 and A7-1
C2C12, 48h

Osteogenic medium for 6 days
10 ng/ml of rhBMP2 for 3 days

C2C12: trans-differentiation model

Glial cell culture medium (Day 4)

ADHESIVE PEPTIDE AND USE THEREFOR

CROSS REFERENCE TO RELATED APPLICATION

The present application is a continuation in part application of International Patent Application PCT/KR2016/002864, filed Mar. 22, 2016, which claims the benefit of Korean Patent Application No. 2015-0042167, filed Mar. 26, 2015 in the Korean Intellectual Property Office, the disclosure of which are incorporated herein.

STATEMENT OF SEQUENCING LISTING

The Sequence Listing submitted in text format (Pa) filed on Dec. 6, 2017, named "SequenceListing.txt", created on Dec. 6, 2017 (15.2 KB), is incorporated herein by reference.

BACKGROUND OF THE INVENTION

Field of the Invention

The present disclosure relates to the polypeptides with adhesive properties to various materials of biological or non-biological origin.

Description of the Related Art

Bio-adhesives are polymeric materials that act as adhesives for cells, tissues or any derivatives derived therefrom and have many practical applications in a variety of fields. For example, they may find applications in medical fields for attaching between tissues or tissues and cells, for healing wounds, regenerating or repair tissues, or in biotechnology for culturing stem cells or other cells in general, delivering drugs acting as carriers, for bio-conjugation or tissue fillers and the like.

Thus bio-adhesives are required to have less side effects and longer half-life adequate for safe and long term use in the body in addition to good adhesiveness.

Examples of bio-adhesive include cyanoacrylate, fibrin, gelatin, albumin or polyurethane based materials. Cyanoacrylates are usually used for local wound closure; however the use is limited by toxic materials released therefrom. Bio-adhesives based on synthetic polymers also have shortcomings due to their weak adhesiveness in aqueous conditions. US Patent Application Publication 2002-0022588 and WO99/66964 disclose albumin or gelatin crosslinked to carbodiimides. However the carbodiimides used for crosslinking are toxic and have weak adhesiveness, thus limiting its use in vivo.

Accordingly, there are needs to develop new bio-adhesive with improved adhesiveness as well as less toxicity applicable in various conditions, particularly in vivo.

SUMMARY OF THE INVENTION

The present disclosure is to provide novel polypeptides with improved adhesiveness with less or no toxicity having wide applications under various conditions and use thereof.

In one aspect, the present disclosure provides for a peptide or its derivative having Formula I: $[X^1\text{-}X^2\text{-}X^3\text{-}X^4\text{-}X^5]_m$:
in which:
$X^1$ is any amino acid,
$X^2$, $X^3$ and $X^4$, which may be identical or different, are each L, V, I, E or A,
$X^5$ is K or R, m is an integer from 1 to 5, and if n is 2 or more, each peptide may be identical or different, or alternatively, $[X^1\text{-}X^2\text{-}X^3\text{-}X^4]$ may be present in multiple copies, wherein the amino acid is a natural or non-natural L- or D-form.

In one embodiment, $X^1$ of formula I is S, T, C, P, N or Q.

In other embodiment, the sequence of $X^2\text{-}X^3\text{-}X^4$ of formula I may be represented by AAA, EEE, LVA, LVL, LVV, LLA, LLL, or LLV.

In other embodiment, the sequence of the peptide of formula I may be represented by QLVVK (SEQ ID NO: 1), QEEEK (SEQ ID NO: 2), QAAAK (SEQ ID NO: 3), NLVVK (SEQ ID NO: 4), or SLVVK (SEQ ID NO: 5).

In other aspect of the present disclosure, there are provided a peptides of Formula II, and Formula I further comprising at its N-term or C-term or both of N- and C-term, [Formula II]: $[X^6\text{-}X^7\text{-}X^8\text{-}X^9\text{-}X^{10}\text{-}X^{11}]n$:
in formula II,
$X^6$ is F, Y or W;
$X^7$ is K or R,
$X^8$ is A, M or I,
$X^9$ is L, M or G,
$X^{10}$ is any amino acid,
$X^{11}$ is C, S or T,
n is 1 or 2,
wherein $X^8$ and $X^9$ together as a group and/or $X^{th}$ and $X^{11}$ together as another group may be absent,
wherein at least one of $X^2$, $X^3$ and $X^4$ of Formula I may be absent.

In one embodiment, the polypeptide of Formula II may be represented by FRALPC (SEQ ID NO: 6), FREEPC (SEQ ID NO: 7), FRVVPC (SEQ ID NO: 8), FEALPC (SEQ ID NO: 9), YRALPC (SEQ ID NO: 10), WRALPC (SEQ ID NO: 11), FRALP (SEQ ID NO: 12), FRAL(SEQ ID NO: 13), or FRPC (SEQ ID NO: 14).

In a further aspect of the present disclosure, the polypeptide of formula I, formula II, or formula I-II may further comprise at their N- and/or C-term a polypeptide of Formula III: $X^{12}_{1\text{-}15}$, in which the polypeptides of Formula I, II and III may be linked in the order of Formula or III-I from N- to C-term, wherein X is positively or negatively charged amino acid. In one embodiment, the positively charged amino acid is K or R, and the negatively charged amino acid is D or E.

In one embodiment of the present disclosure, there are also provided isolated polypeptides having an amino acid sequence consisting of the amino acid sequence as set forth in SEQ ID NO: 1, 6, 15-22, 24-27, 29-37, 42-64, 67 or 68.

When the present polypeptide starts with formula III, such as formula III-I, or the first amino acid may be positively or negative charged. When the present polypeptide starts with formula III, the first amino acid may be positively or negative charged, which are also encompassed in the present disclosure, Also provided in the present disclosure is the polypeptides that are modified at its N- or C- or both N- and C-term with a non-reactive or an inert group for various purposed.

Also provided in the present disclosure are nucleotide sequences encoding the present polypeptides, and vectors comprising the same, and eukaryotic or prokaryotic cells transformed with the vectors.

The polypeptides of the present disclosure may be conjugated to a various agents for targeting or labeling as desired depending on a particular purpose.

In still other aspect, the present disclosure provide for a bio-conjugating composition comprising the present polypeptide as disclosed herein.

In still other aspect, the present disclosure provide for an adhesive composition for attaching or improving adhesiveness of various material to other various materials of biological or non-biological origin.

In still other aspect, the present disclosure provide for a use of the present peptide for bio-conjugation.

In still other aspect, the present disclosure provide for a use of the present peptide for attaching or improving adhesiveness of or attaching various materials to other various materials of biological or non-biological origin.

In still other aspect, the present disclosure provide for a use of the present polypeptide for cell attachment.

Advantageous Effects

Novel peptides of the present disclosure can be advantageously used as a bio-adhesive for attaching biological materials such as cells or tissues to various surfaces. Also the present peptides may be used as being conjugated to various inorganic or organic materials such as nucleic acids, proteins, carbohydrates, or lipids and the like for attaching them to various surfaces and thus may find many applications in the fields in need thereof.

BRIEF DESCRIPTION OF THE DRAWINGS

In FIG. 1A, the peptides according one embodiment of the present disclosure conjugated to biotin via a disulfide bond were attached to a glass and the signal from the biotin was analyzed. The signal indicates that the present peptides are attached to the glass. The signal was disappeared when it was treated with DTT to remove disulfide bond indicating that the signals were from the biotin conjugated to the present peptides.

FIG. 1B is a schematical representation of the method employed in FIG. 1A, showing that the present peptides attached to the glass are conjugated to a biotin, which is then detected by an antibody to the biotin. The signal is disappeared by treatment with DTT that removes the SH bond and thus releases the biotin from the present peptides.

FIG. 1C is a schematical representation of the method to test the adhesiveness of the present peptide to various non-biological materials, which are basically identical to FIG. 1A except that FITC(fluorescein isothiocyanate) is used instead of biotin as a labeling agent.

FIG. 1D is the results of the analysis performed as described in FIG. 1C and shows the adhesiveness of the present peptides to various surfaces of non-biological materials. From left to right, the circles on each of the panel indicate PBS (phosphate buffer saline) only, FITC-conjugated A7-1, and FITC dye only, respectively.

FIG. 4A is the results showing that increasing adhesiveness of the cells by A7-1 does not require the treatment of the cells with electrolytes (EDTA treatment) and also do not require new protein synthesis (CHX treatment). However the adhesiveness was inhibited at an early stage by treatment of the cell with serum. This may be explained that various types of GAGs abundantly present in the serum firstly or preferentially bind to the present peptides, leaving less amount to the cells.

FIG. 4B is the results of testing the involvement of GAG or collagen in the mechanism of promoting the adhesiveness by the present peptides. The results show that both GAG and collagen are involved in the mechanism of promoting cell adhesiveness by the present peptides, evidenced by the results that the adhesiveness was disappeared when the cells were treated with enzymes to remove potential targets. The decrease in the cell adhesiveness by treating cells with collagenase indicates that the increase in the adhesiveness is partly due to the interaction with the collagen. And the results from treatment with hyaluronidase indicate that the hydrolysis of heparin sulfate, thus the interaction between heparin sulfate in GAG and the present peptides, is also at least partly responsible for promoting the adhesiveness by the present peptides. A graph in the lower part id the results testing the involvement of GAG and shows that the adhesiveness increased by the present peptide A7-1 is significantly decreased in a concentration dependent manner by the addition of heparin and C-sulfate (CS). This indicates that GAGs are involved in the adhesiveness by the present peptide A7-1. The changes in the concentration of GAG are known to be related to the development of various diseases. Thus the present peptide may be utilized to control GAG concentration in blood or as drug carrier targeting GAG.

FIG. 4C is the results to test the present peptide adhesiveness in the presence of soluble RGDS peptides as a competitor and shows that in the absence of A7-1, the addition of RGDS significantly reduces the adhesiveness of the cells to the bottom because RGDS firstly or preferentially binds to adhesive molecule integrins. However, in the presence of A7-1, it is found that the cell adhesiveness is not affected by the addition of RGDS. This indicates that the present peptides have a distinct mechanism different from that of an anchorage dependent adhesiveness via integrin.

FIG. 9A is the results of comparing the adhesiveness of the present peptide A7-1 with that of Laminin and Poly-L-Ornithin in which nerve cells from a spinal cord were incubated in the culture plates coated with each of the peptides above and CCK-8 was examined at the hours indicated in the figure.

FIG. 9B is the result of microscopic examination at day 4 after the culture.

FIG. 9C is the results of experiment to confirm that the primary cells coated with the present peptide A7-1 are indeed the cells originated from the nerve, in which protein markers specific for nerve cells were examined by immunofluorescence followed by a confocal microscopy. The results indicate that the present peptides have superior adhesiveness compared to the other known adhesive peptides.

FIG. 10A is the results showing that numerous actin-rings, a sign that the cells are in an early stage of adhesiveness, were observed in negative control cells in contrast to the cells treated with the present peptide A7-1 in which numerous stress fiber formations were observed indicating that the cells are in an advanced stage of adhesiveness.

FIG. 10B is a graph quantifying the results of FIG. 10A.

FIG. 10C is the results of measuring the geometric shape of the cells (cell aspect ratio: cells longitudinal/horizontal ratio, in which the value of the cells in a perfect round shape in an very early stage during the process of adhesiveness is near 1, and is increasing as the cells are attaching). The results show that the cells treated with A7-1 have an excellent adhesiveness compared to the control.

DETAILED DESCRIPTION OF THE INVENTION

Definitions

Figure 1A:
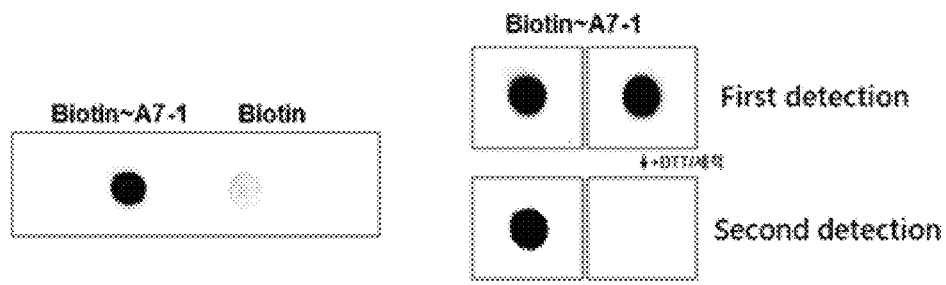
FIGS. 1A to 1D are results showing the adhesiveness of the peptide (A7-1) according to one embodiment of the present disclosure to glass, Zr, Vinyl, Polystyrene fiber, Polycaprolactone, Ti and Collagen (Col) as non-biological materials.
Figure 1B:
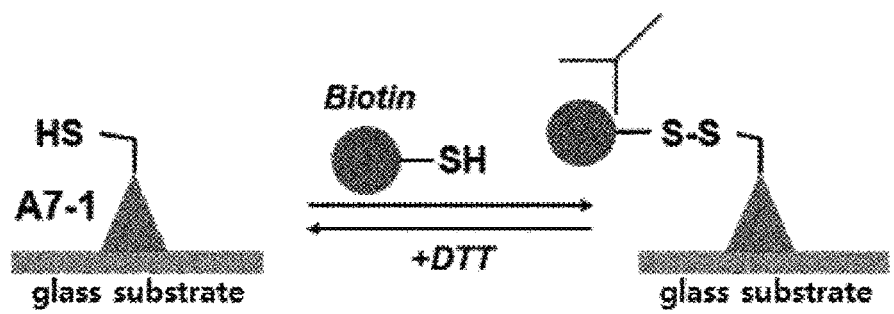
Figure 1C:
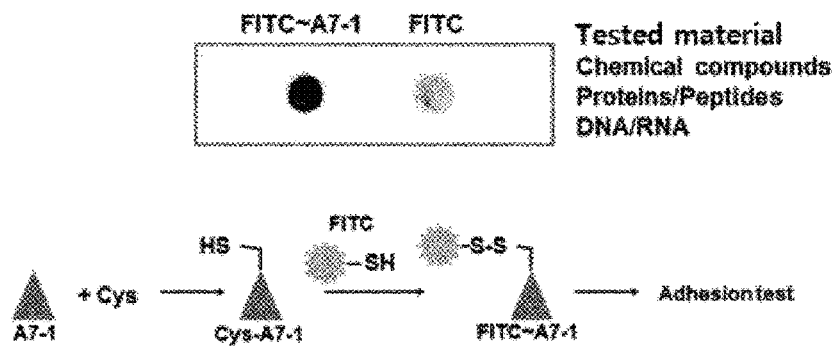
Figure 1D:
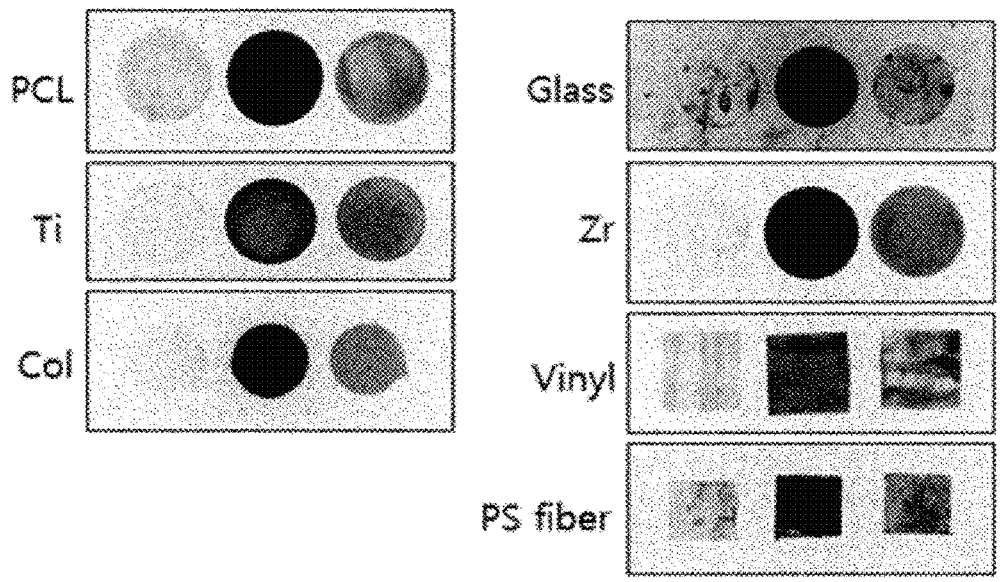
Figure 2A:
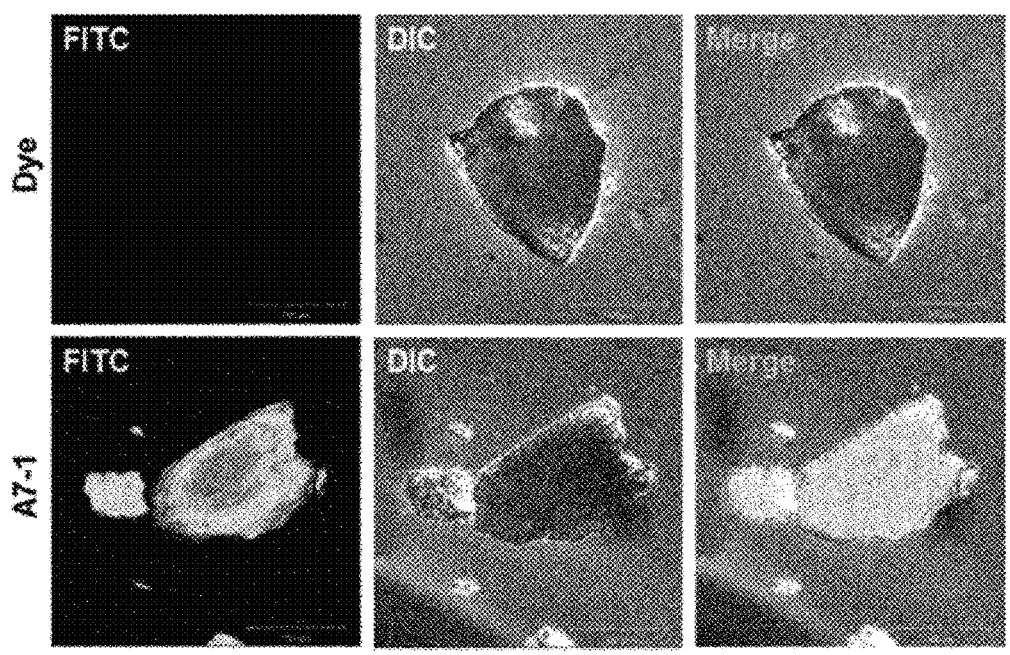
FIG. 2A is the results of testing the adhesiveness of the present peptide conjugated to FITC to the surface of bone graft Bio-OSS® (Geistlich Pharma, Inc), showing the excellent adhesiveness of the present peptide to a commercial bone graft.
Figure 2B:
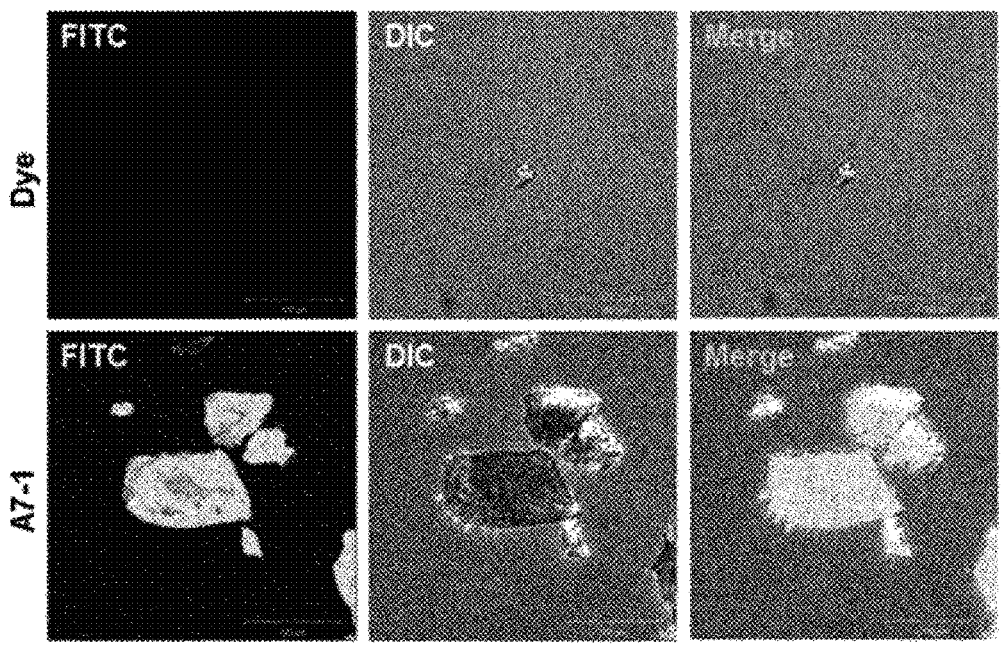
FIG. 2B is the results of testing the adhesiveness of the present peptide conjugated to FITC to the surface of bone graft MBCP™ (Biomatlante) and shows the excellent adhesiveness of the present peptide to a commercial bone graft. The fluorescent microscope image was taken at X200.
Figure 2C:
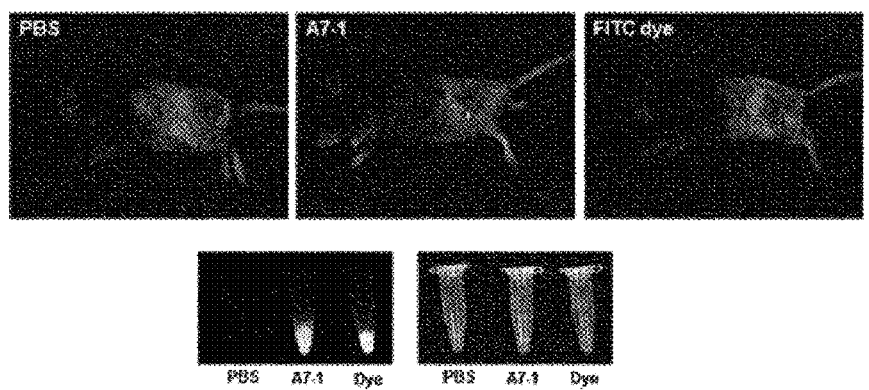
FIG. 2C is the results of testing the adhesiveness of the present peptide conjugated to a FITC to atrial cartilaginous tissue/cells of mice, in which the mice were injected with PBS, FITC-conjugated A7-1, or FITC at the cartilaginous tissue. The mice were sacrificed and the tissues were examined with a fluorescent image analyzer. The fluorescence signals were detected only in the cartilaginous tissue injected with the present peptides. This indicates that the present peptides also have excellent adhesiveness to cartilaginous tissue (*), the major components of which are GAG (glycoaminoglycan) including heparan sulfate, heparin, or chondroitin sulfate and the like. The results correspond to the results of FIG. 4B.
Figure 2D:
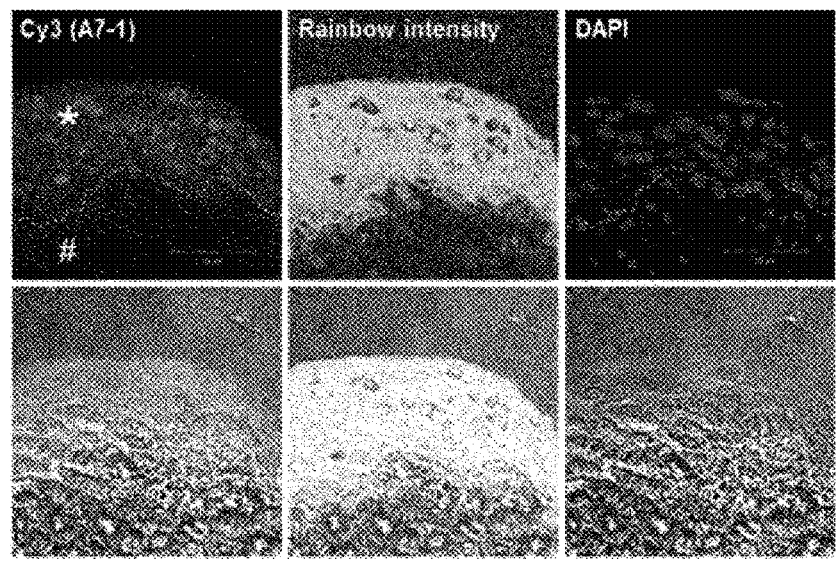
FIG. 2D is the results of testing the adhesiveness of the present peptide conjugated to Cy to atrial cartilaginous tissue/cells in mice, in which mice were injected with PBS, Cy-conjugated A7-1, or Cy at cartilaginous tissue. The mice were sacrificed and the tissues were examined with a confocal image analyzer. The fluorescence signals were detected only in the cartilaginous tissue injected with the present peptides. This indicates that the present peptides have excellent adhesiveness to cartilaginous tissue (*) and bone (#), corresponding to the results of FIG. 4B.
Figure 2E:
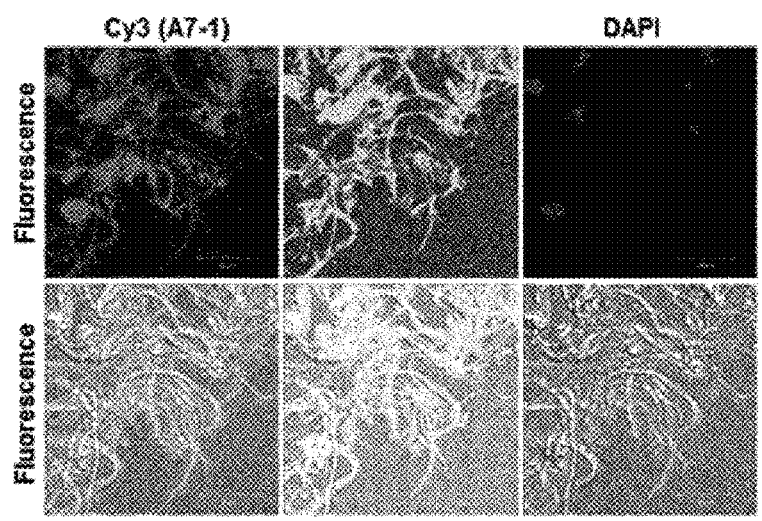
FIG. 2E is the results of the test performed basically in the same manner as described for FIG. 2D except that the tissues from the mice injected with the present peptide were disintegrated and fixed and examined by a confocal image analyzer. The results show that the present peptides have an excellent adhesiveness to elastic fibers which are known to comprise large amount of GAG or ECM (Extracellular matrix). This corresponds to the result of FIG. 4B described below.
Figure 2F:
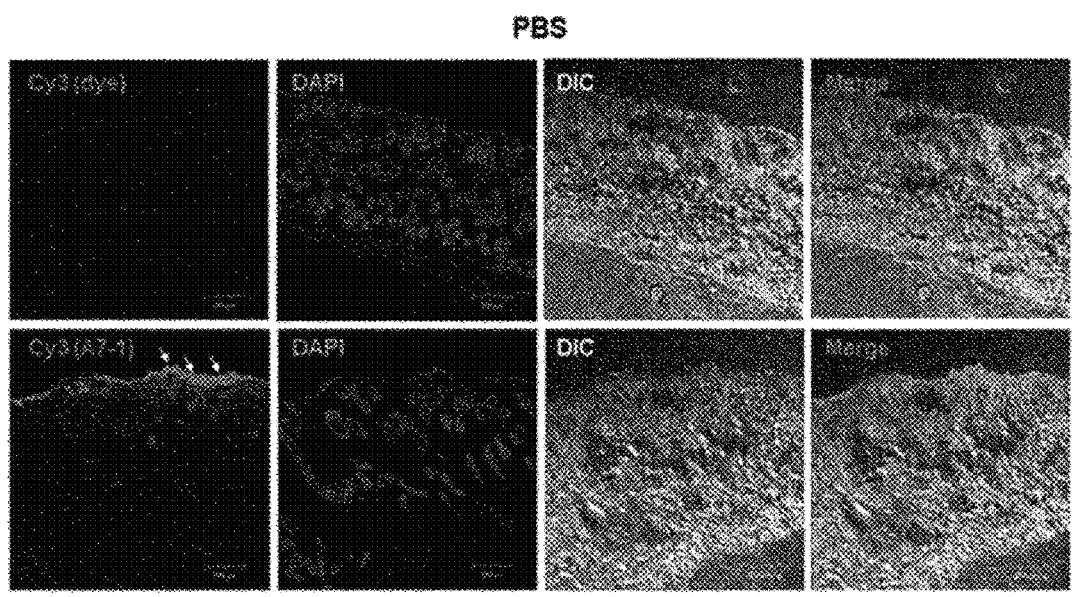
FIG. 2F is the results of the test performed basically in the same manner as described for FIG. 2E except that the present peptides were applied to the skin of mice. The results show that the present peptides have an excellent adhesiveness to skin which is known to contain large amount of elastic fibers and ECM of the skin (epidermis and dermis). This corresponds to the result of FIG. 4B described below.
Figure 2G:
FIG. 2G is the results of the test performed basically in the same manner as described for FIG. 2F except that the present peptides were applied to the hair of mice. The results show that the present peptides have an excellent adhesiveness to hair which is known to contain large amount of elastic fibers. This corresponds to the result of FIG. 4B described below.
Figure 2H:
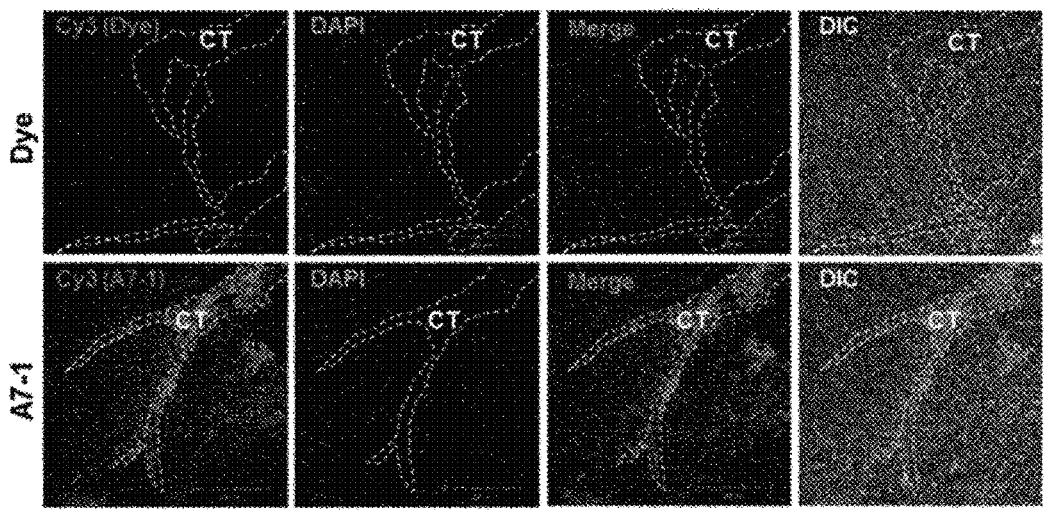
FIG. 2H is the results of the test performed basically in the same manner as described for FIG. 2F except that the present peptides were applied to the hypodermic fat of mice and shows an excellent adhesiveness to the connective tissue (CT).
Figure 2I:
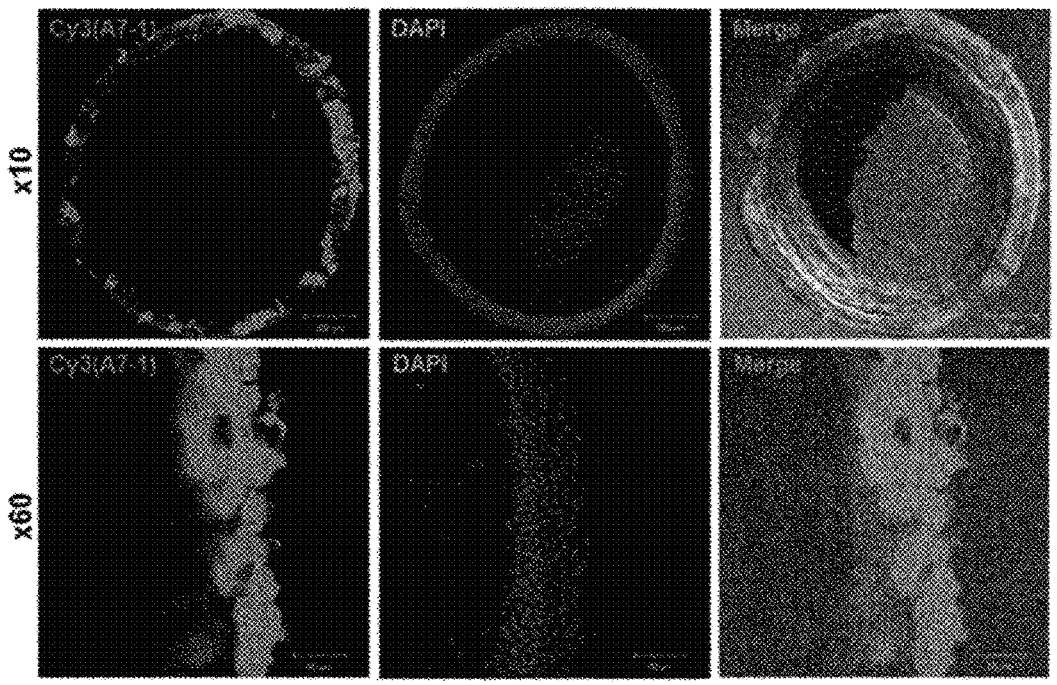
FIG. 2I is the results of the test performed basically in the same manner as described for FIG. 2F except that the present peptides were applied to the eye ball of mice and shows the strong coloration on the surface of the eye ball 30 min after the treatment. This indicates the excellent adhesiveness of the present peptide to collagen.
Figure 2J:
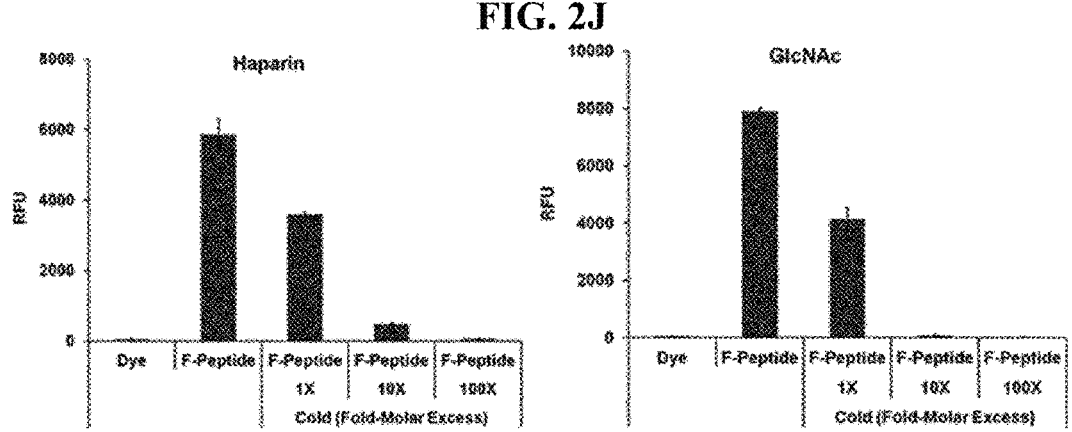
FIG. 2J is the results of testing the affinity of the present peptide labelled with FITC to heparin or N-acetylglucosamine by affinity chromatography using beads linked to the heparin or N-acetylglucosamine. The results show that the addition of un-labelled cold peptides cause a sudden decrease of the FITC signal, indicating the adhesiveness of the present peptide to the tested material. The results also indicate that the present peptide having adhesiveness/binding affinity to heparin can be used to lessen the anticoagulant effect of heparin, or to increase the accessibility to extracellular matrix by binding to growth factors.
Figure 2K:
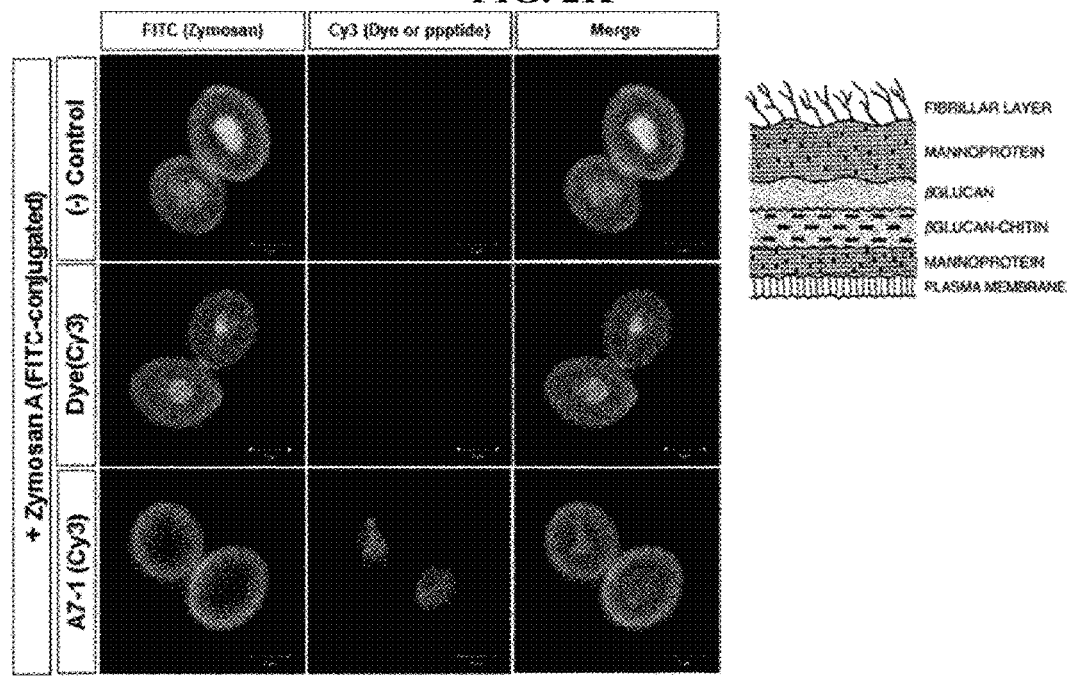
FIG. 2K is the result of testing the adhesiveness of the present peptide to Chitin (GlcNAc) and beta (1,3) glucan, in which the peptides were labelled with Cy and examined with a fluorescent microscopy. The results show the accumulation of the present peptides to zymosan particles labelled with FITC. Zymosan particles are comprised of Chitin (GlcNAc) and beta (1,3) glucan and are components of yeast cell wall. Chitin is a polymer of N-acetylglucosamines, and beta (1,3) glucan is a polymer of glucoses.
Figure 2L:
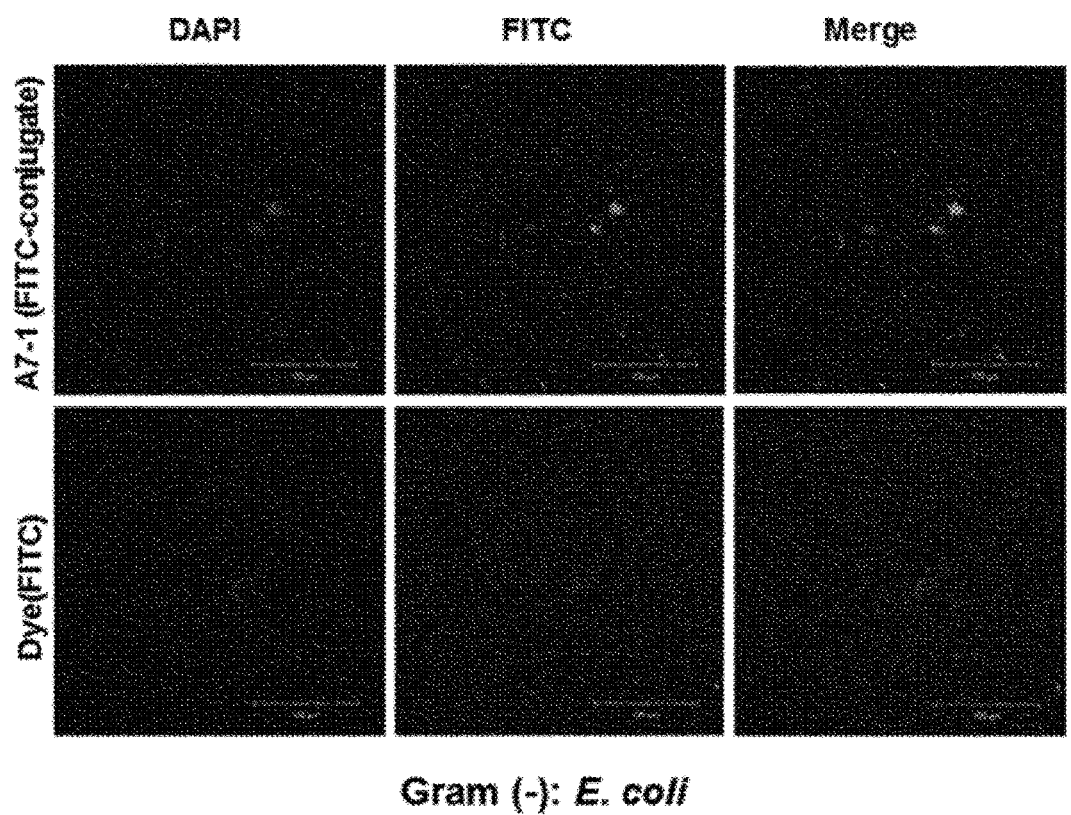
FIG. 2L is the results showing the adhesiveness of the present peptide to the cell wall of gram negative bacteria. The major component of the cell wall is proteoglycan consisting of GlcNAc (N-acetylglucosamine) and MurNAc (N-acetylmuramic acid). The results were examined by fluorescence microscopy and the counter staining was done with DAPI.
Figure 2M:
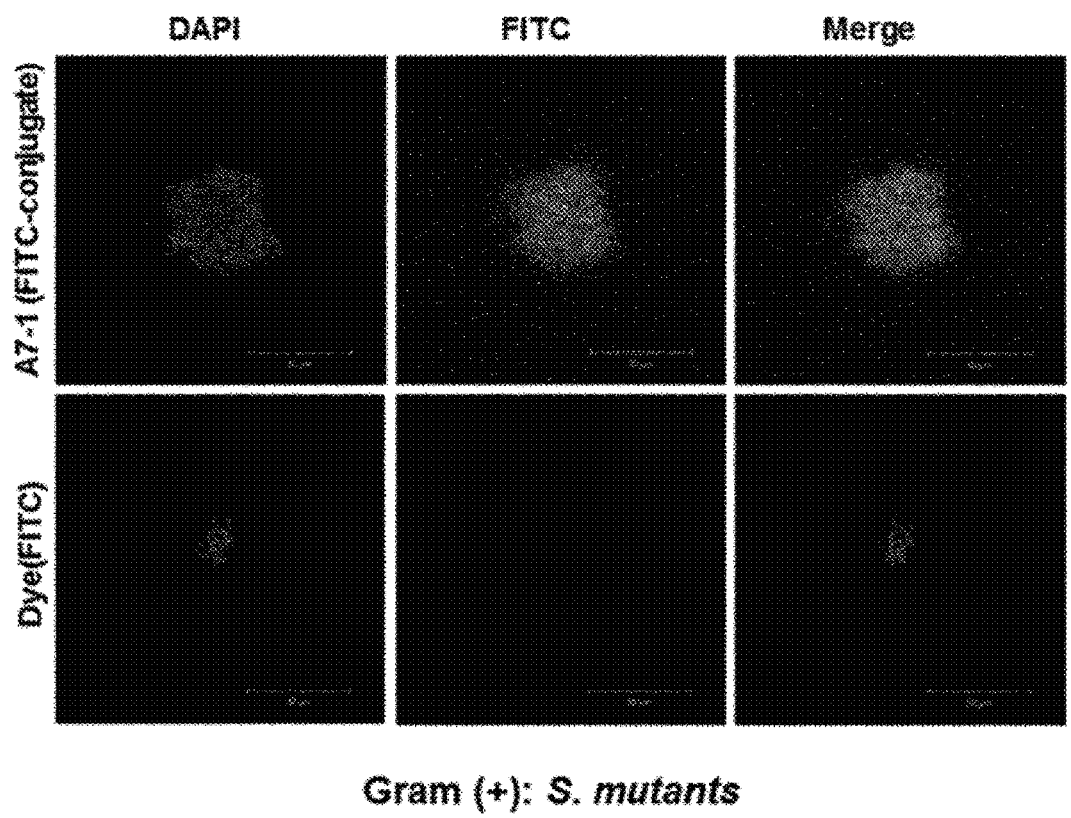
FIG. 2M is the results showing the adhesiveness of the present peptide to the cell wall of gram positive bacteria. The major component of the cell wall is proteoglycan consisting of GlcNAc (N-acetylglucosamine) and MurNAc (N-acetylmuramic acid). The results were examined by fluorescence microscopy and the counter staining was done with DAPI.
Figure 3A:
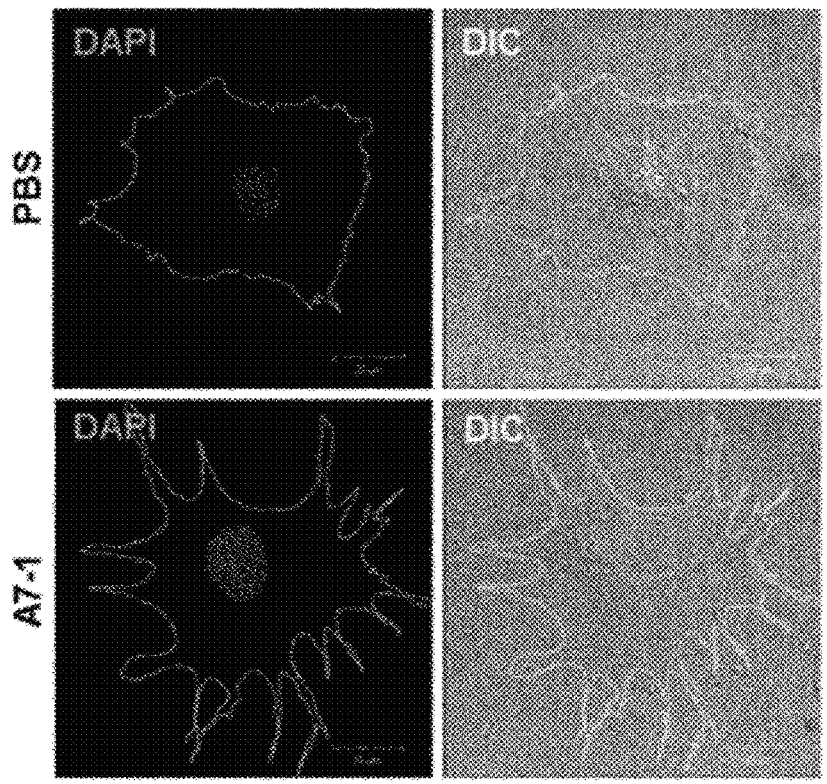
FIG. 3A is the results of testing the ability of the present peptide to increase the adhesiveness of anchorage dependent cell MC3T3-E1 to culture plates. The results show that the cells treated with the present peptide have a rough membrane boundary compared to negative control treated with PBS only. This indicates that the present peptide can increase the adhesiveness of biological materials such as cells to non-biological materials such as culture plates.
Figure 3B:
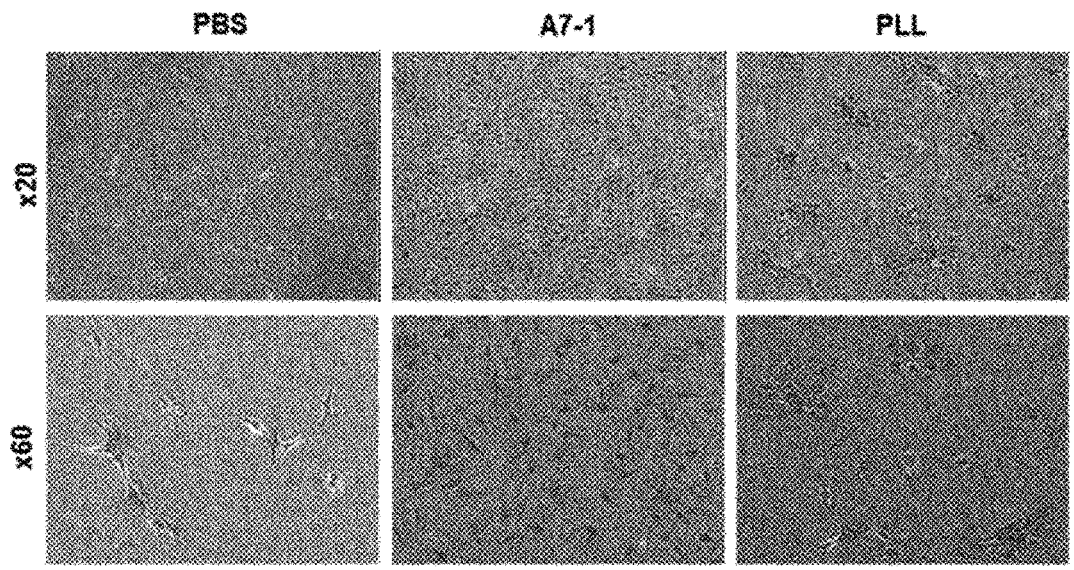
FIG. 3B is the results of testing the adhesiveness of anchorage dependent cell MC3T3-E1 treated with the present peptide to hydrophobic culture plates in comparison to those treated with PLL(poly-L-lysin) currently used to increase the adhesiveness of cells. The results show that the cells treated with the present peptides have increased adhesiveness in comparison to the cells treated with PBS or PLL. This indicates that the present peptides can have an industrial applicability by complement the low adhesiveness of various currently used tissue implant material such as PCL.
Figure 3C:
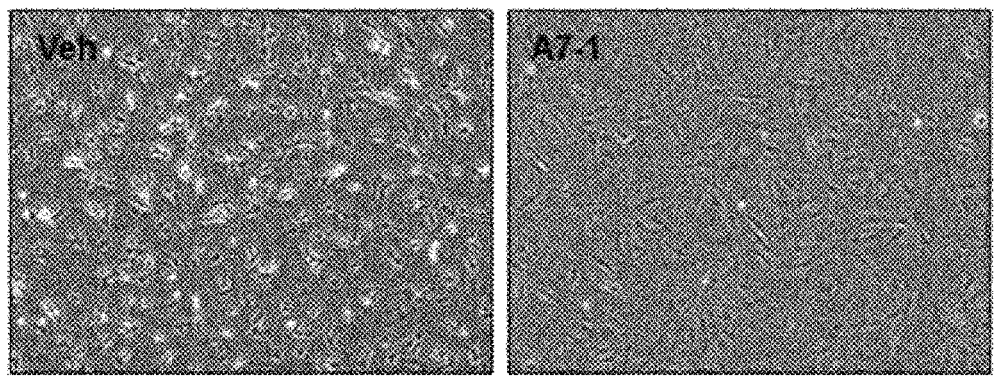
FIG. 3C is the results of testing the adhesiveness of anchorage dependent cell ST2 treated with the present peptide to hydrophobic culture plates in comparison to control treated only with a buffer. The results show that the cells treated with the present peptide have an increased adhesiveness compared to the control as shown by the fluorescent miscopy analysis.
Figure 3D:
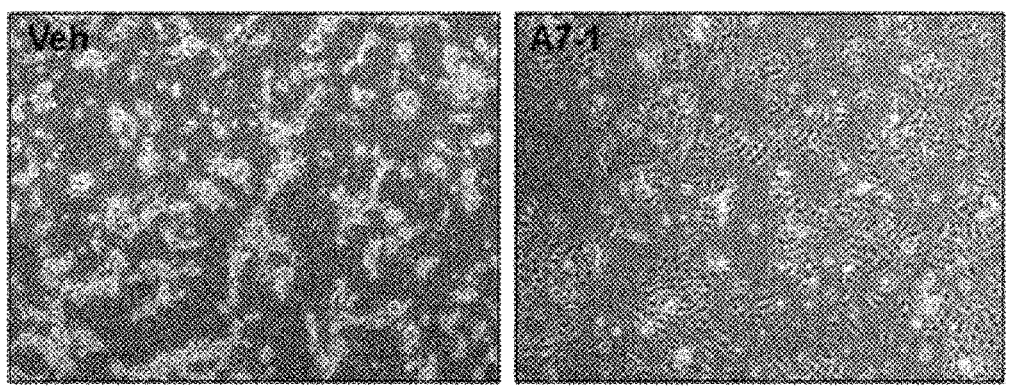
FIG. 3D is the results of testing the adhesiveness of anchorage dependent cell C2C12 treated with the present peptide to culture plates after the cells were thawed from freezing. The results show that the cells treated with the present peptide have an increased adhesiveness compared to the control as shown by the fluorescent miscopy analysis. Particularly the adhesiveness of cells after thawing is known to have great impact on the survival of the cells. The results indicate that the present peptides can be advantageously used in the field of cell culture particularly in the field of primary cell culture, by minimizing the cell death after the cells are thawed.
Figure 3E:
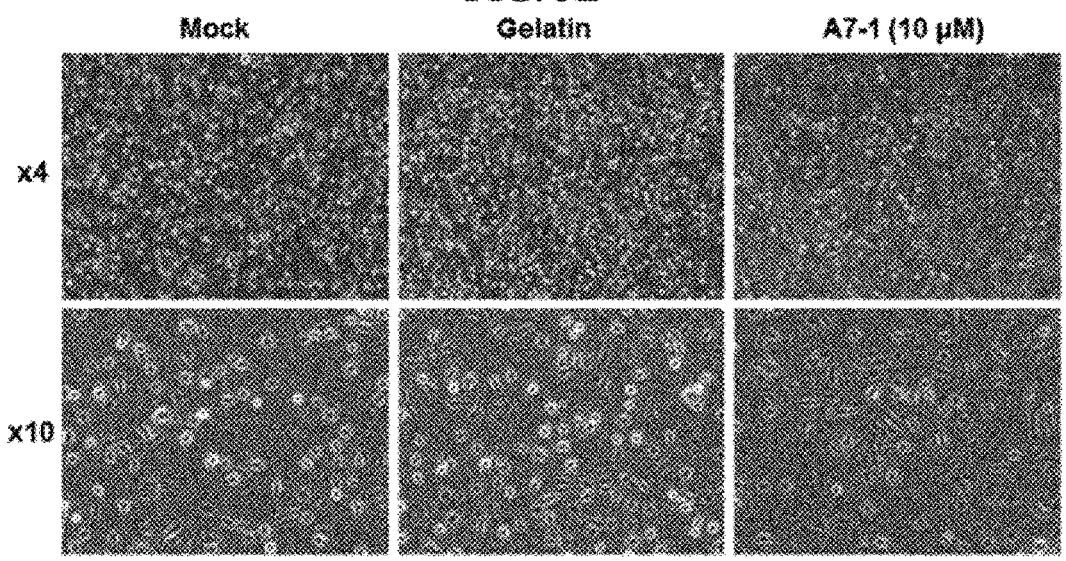
FIG. 3E is the results of testing the adhesiveness of mitomycin treated STO feeder cells treated with the present peptide to hydrophilic culture plates in comparison to a Mock as a negative control and gelatin. The results show that the cells treated with the present peptide have an increased adhesiveness compared to the negative control and gelatin control as shown by the fluorescent miscopy analysis.
Figure 3F:
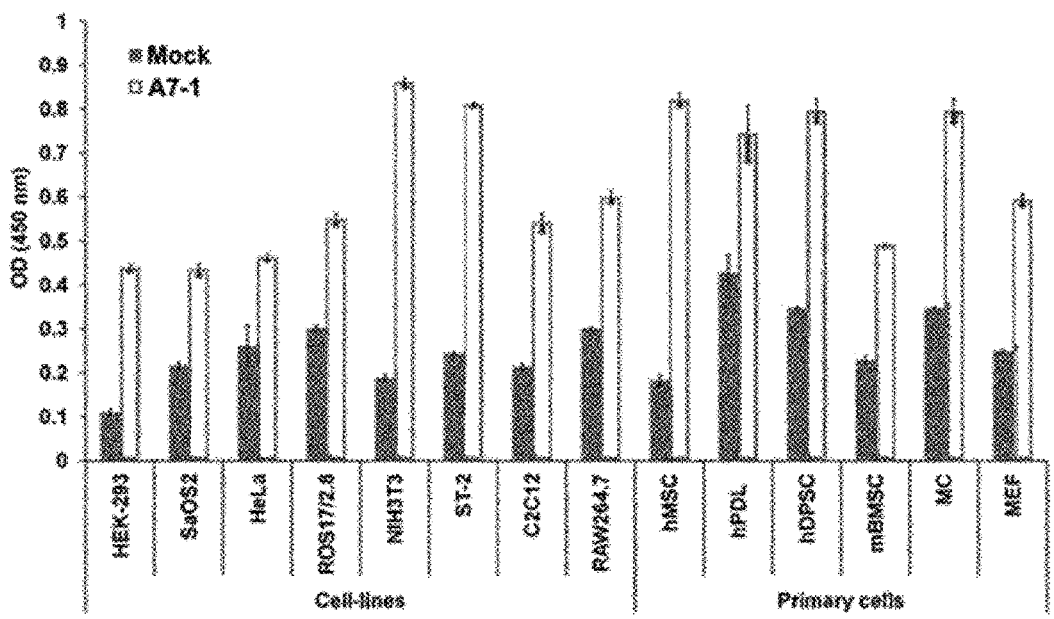
FIG. 3F is the results of testing the ability of the present peptide to increase the adhesiveness of various cells (established cell lines and primary cells) as indicated in the figure to hydrophobic culture plates in comparison to negative control (Mock). The results were analyzed by measuring the cell metabolism. The results show that the present peptide can increase the adhesiveness of various cells compared to the negative control.

In the present disclosure, amino acids are denoted by single letter code defined in the related art as follows: A, Alanine; R, Arginine; N, Asparagine; D, Aspartic acid; C, Cysteine; E, Glutamic acid; Q, Glutamine; G, Glycine; H, Histidine; I, Isoleucine; L, Leucine; K, Lysine; M, Methionine; F, Phenylalanine; P, Proline; S, Serine; T, Threonine; W, Tryptophan; Y, Tyrosine; V, Valine; Z, Glutamic acid and Glutamine; X, any amino acid in Sequence listing.

As used herein the term "amino acid" refers to naturally occurring 20 amino acids or non-natural amino acids, as well as post translationally modified amino acids, amino acid analogs and amino acid mimetics that function in a manner similar to the naturally occurring amino acids, including for example, phosphoserine and phosphothreonine; rare amino acids such as 2-aminoadipic acid, hydroxylysine, norvaline and norleucine; amino acids modified to improve their stability in cell and cell penetration; and optical isomers of D- and L-form. Positively charged amino acids, negatively charged amino acids, polar non-charged amino acids, and non-polar aliphatic amino acids, which may be used in the present disclosure, are well known in the art and may be selected by one of ordinary person in the art without difficulty.

As used herein, the terms "natural and non-natural" each refers to the compounds found in cells, tissues or bodies; and the compounds artificially modified thereto for a particular purpose, respectively.

As used herein, the term "peptides" and "polypeptides" are interchangeably used, and are read from N- to C-term unless defined otherwise and refer to a molecule in which amino acid monomers are covalently linked to each other, and are interpreted to include peptides comprised of native amino acids or their lysed products, synthetic peptides, peptides prepared in a recombinant manner, peptide mimetics (typically synthetic peptide), analogous such as peptoide and semipeptoids, and peptides modified to improve/change their function such as stability in cells. Examples of the modification include a N-term modification, a C-term modification, a peptide bond modification such as $CH_2$—NH, $CH_2$—S, $CH_2$—S=O and $CH_2$—$CH_2$, a back-bone modification, and side-chain modification. Peptide mimetics are prepared by methods known in the art, which may be referred to, for example, Quantitative Drug Design, C. A. Ramsden Gd., Choplin Pergamon Press (1992).

As used herein the term "adhesion" includes attachment or adsorption, including reversible or irreversible adhesion. In other aspects, the adhesion includes attachment or adsorption through at least one of chemical interactions including covalent bonds, ionic bonds, van der waals bonds, and hydrogen bonds.

In the present disclosure, inorganic materials or the surface of inorganic materials are used interchangeably. Inorganic materials include materials within the generally accepted meaning which do not contain carbon, silicon or nitrogen, or have a relatively free electron configuration due to high degree of electrostatic conductivity. Particularly included in the present disclosure are inorganic materials having a hydrophobic surface such as metal for example iron, copper, or noble metal including gold, silver or platinum, titanium, or aluminum; ceramics such as zirconia; calcium apatite crystals such as hydroxyl apatite; high molecular weight synthetic resins such as polyethylene and; glass and combinations thereof without being limited thereto.

The term "surface" as used herein is interpreted in the broadest sense and to be present in the materials having at least 2 dimensional structures without being limited to materials having particular shape and/or sizes. Also the surface at the molecular or unit level, and the surfaces formed by the materials comprised of such molecules or units are included. For example the surfaces included in the present disclosure can be found/present in particles in sizes ranging from few nanometer to few micrometer or materials in sizes ranging from few millimeters to few meters.

The present peptides

In one aspect, the present disclosure relates to a peptide or polypeptides or derivatives thereof having Formula I: $[X^1-X^2-X^3-X^4-X^5]_m$:

in which $X^1$ is any amino acid, $X^2$, $X^3$ and $X^4$, which may be identical or different, are each L, V, I, E or A, $X^5$ is K or R, n is an integer from 1 to 5, if n is 2 or more, each polypeptide may be identical or different, wherein the amino acid is a natural or non-natural D- or L-form residue.

In one embodiment of the present disclosure, polar non-charged amino acids are S, T, C, P, N or Q.

In the present disclosure, the peptide of formula I, also referred as a first domain/region, is found to be involved in the adhesion to cell surfaces or cell membranes and also can be present in multiple numbers depending on the particular applications of interest as described herein. Further the first region is considered a core region which may affect the secondary structure of the present peptides and assists in maintaining the molecular characteristics of the other regions as described below. Particularly the first region is hydrophobic in nature enabling hydrophobic interactions with molecules or cells of interest, and can be used advantageously for tissue regeneration for example being provided as nanostructured supports or a component of gels.

In the present disclosure, one or more of the first region or the peptide of formula I may be comprised in the present peptides and when more than one is present, each one may be identical or different. The number of formula I included in the present peptides may be various and determined in consideration of the functionalization of interest of the present peptide such as for use in the preparation, storage or delivery, or in consideration of the effects or various applications as described hereinafter. For example, in formula I, n may be 1 to 10, 1 to 9, 1 to 7, 1 to 6, 1 to 5, 1 to 4, 1 to 3, 1 to 2, or 1.

In one embodiment of formula I, $X^1$ is any amino acids, particularly polar non-charged amino acids, more particularly S, T, C, P, N or Q.

In other embodiment of formula I, $X^2$, $X^3$ and $X^4$, which may be identical or different, and each are L, V, I, E or A. The sequence of $X^2$-$X^3$-$X^4$ are for example AAA, EEE, LVA, LVL, LVV, LLA, LLL, or LLV and the like without being limited thereto. In other embodiment, the formula I may be $X^1$-LVV-$X^5$, $X^1$-AAA-$X^5$ or $X^1$-EEE-$X^5$.

In one embodiment, the sequence of formula I is represented by QLVVK (SEQ ID NO: 1), QEEEK (SEQ ID NO: 2), QAAAK (SEQ ID NO: 3), NLVVK (SEQ ID NO: 4) or SLVVK (SEQ ID NO: 5).

In other aspect, the present disclosure relates to a peptide of formula II or a peptide of formula I further comprising formula II: $[X^6-X^7-X^8-X^9-X^{10}-X^{11}]n$, in formula II, $X^6$ is any one of F, Y and W, $X^7$ is K or R, $X^8$ is any one of A, M and I $X^9$ is any one of L, M and G, $X^{10}$ is any amino acid, $X^{11}$ is any one of C, S and T, wherein at least one group of ($X^7$ and $X^8$) and ($X^{10}$ and $X^{11}$) may be absent, wherein n is 1 or 2.

In one embodiment, the peptide of formula II may be linked to an amino terminal (N-term) or a carboxy terminal (C-term), or both of N- and C-term of formula I.

According to the present disclosure, the peptide of formula II, referred to as a second region/domain, imparts a hydrophilic property to the present peptides enabling easy dissociation and may form an alpha helix as a secondary structure when it is present as a single molecule in combination with the peptide of formula I.

In one embodiment, at least one of the peptide of formula I and formula II each may be included in the present peptide in various arrangements. For example, the present peptides may include a peptide in which at least one of peptide of formula I being connected to at least one of peptide of formula II, including for example a peptide of formula I-II, a peptide of formula II-I, a peptide of formula I-I-formula II-II, or in which at least two of consecutively connected peptides of formula I and II are further linked, including for example a peptide of formula I-II-I-II, or formula I-II-I, or formula II-I-II. The order may be changed.

In one embodiment of the present disclosure, the peptide of formula II is represented by FRALPC (SEQ ID NO: 6), FREEPC (SEQ ID NO: 7), FRVVPC (SEQ ID NO: 8), FEALPC (SEQ ID NO: 9), YRALPC (SEQ ID NO: 10), WRALPC (SEQ ID NO: 11), FRALP (SEQ ID NO: 12), FRAL (SEQ ID NO: 13), or FRPC (SEQ ID NO: 14).

In other aspect of the present disclosure, the peptide of formula I, II or the peptide including both formula I and II may further comprise a peptide of formula III: $X^{12}_{1-15}$ at its N- or C-term, including such as formula wherein $X^{12}$ is positively or negatively charged amino acids.

It is found in the present disclosure that charged amino acid(s) are required for formula III, particularly when present at N-term for proper function of the present peptides.

In one embodiment, in formula III, the positively charged amino acid is K or R.

In other embodiment, in formula III, the negatively charged amino acid is D or E.

In one embodiment of the present disclosure, the present peptides encompassed by formula I, formula II, or formula I and II, or each in combination with formula III that is linked at the N-term may be represented by: QLVVK (SEQ ID NO: 1), FRALPC (SEQ ID NO: 6), RQLVVK (SEQ ID NO: 15); FRALPCRQLVVK (SEQ ID NO: 16); RQLVVKFRALPC (SEQ ID NO: 17); RQLVVKFRALPCRQLVVKFRALPC (SEQ ID NO: 18); RQLVVKFRALP (SEQ ID NO: 19); RQLVVKFRAL (SEQ ID NO: 20); KQLVVKFRALPC (SEQ ID NO: 21); RQKFRALPC (SEQ ID NO: 22); RQEEEKFRALPC (SEQ ID NO: 23); RQAAAKFRALPC (SEQ ID NO: 24); RQLVVKFRPC (SEQ ID NO: 25); RQLVVKFREEPC (SEQ ID NO: 26); RQLVVKFRVVPC (SEQ ID NO: 27); RQEEEKFREEPC (SEQ ID NO: 28); EQLVVEFEALPC (SEQ ID NO: 29); RQLVVKYRALPC (SEQ ID NO: 30); RQLVVKWRALPC (SEQ ID NO: 31); RNLVVKFRALPC (SEQ ID NO: 32); RSLVVKFRALPC (SEQ ID NO: 33); R-(QLVV)$_2$-KFRALPC (SEQ ID NO: 34); R-(QLVV)$_3$-KFRALPC (SEQ ID NO: 35); R-(QLVV)$_4$-KFRALPC (SEQ ID NO: 36); RQLVVK-(FRALPC)$_2$ (SEQ ID NO: 37); (R)$_2$-QLVVKFRALPC (SEQ ID NO: 38); (R)$_5$-QLVVKFRALPC (SEQ ID NO: 39); (R)$_{10}$-QLVVKFRALPC (SEQ ID NO: 40); or (R)$_{15}$-QLVVKFRALPC (SEQ ID NO: 41).

In other embodiment of the present disclosure, the present peptides encompassed by formula I and II in combination with formula III at the N-term may be represented by: RQLVVKFRALPC (SEQ ID NO: 17); KQLVVKFRALPC (SEQ ID NO: 21); RNLVVKFRALPC (SEQ ID NO: 32); RSLVVKFRALPC (SEQ ID NO: 33); RQVVVKFRALPC (SEQ ID NO: 42); RQIVVKFRALPC (SEQ ID NO: 43); RQAVVKFRALPC (SEQ ID NO: 44); RQEVVKFRALPC (SEQ ID NO: 45); RQLLVKFRALPC (SEQ ID NO: 46); RQLIVKFRALPC (SEQ ID NO: 47); RQLAVKFRALPC (SEQ ID NO: 48); RQLEVKFRALPC (SEQ ID NO: 49); RQLVLKFRALPC (SEQ ID NO: 50); RQLVIKFRALPC (SEQ ID NO: 51); RQLVAKFRALPC (SEQ ID NO: 52); RQLVEKFRALPC (SEQ ID NO: 53); RQAAAKFRALPC (SEQ ID NO: 24); RQEEEKFRALPC (SEQ ID NO: 23); RQLVVRFRALPC (SEQ ID NO: 54); RQLVVKYRALPC (SEQ ID NO: 30); RQLVVKWRALPC (SEQ ID NO: 31); RQLVVKFKALPC (SEQ ID NO: 55); RQLVEFEALPC (SEQ ID NO: 56); RQLVVKFRLLPC (SEQ ID NO: 57); RQLVVKFRILPC (SEQ ID NO: 58); RQLVVKFRVLPC (SEQ ID NO: 59); RQLVVKFRELPC (SEQ ID NO: 60); RQLVVKFRAAPC (SEQ ID NO: 61); RQLVVKFRAIPC (SEQ ID NO: 62); RQLVVKFRAVPC (SEQ ID NO: 63); RQLVVKFRAEPC (SEQ ID NO: 64); RQLVVKFRVVPC (SEQ ID NO: 27); RQLVVKFREEPC (SEQ ID NO: 26); RQEEEKFREEPC (SEQ ID NO: 28); RQEEEEFEEEPC (SEQ ID NO: 65); RQLVVKFRALXC (SEQ ID NO: 66); RQLVVKFRALPS (SEQ ID NO: 67); RQLVVKFRALPT (SEQ ID NO: 68); or RQLVVKFRALPX (SEQ ID NO: 69). The peptides disclosed above contain substitution(s) at various positions and were generated based on the 12-mer peptide of SEQ ID NO: 17 in consideration of the experimental results for characterizing the adhesiveness activity of the present peptides and thus it is evident that they also have the adhesiveness activity and thus are encompassed by the present disclosure.

In other embodiment, the present disclosure is related to polypeptides with SEQ ID NO: 1 to 69.

In still one embodiment, the present disclosure is related to an isolated polypeptide having an amino acid sequence as set forth in SEQ ID NO: 1, 6, 15-22, 24-27, 29-37, 42-64, 67 or 68.

In still other embodiment, the N-term amino acid of the present peptide comprising the peptide of formula III at the N-term is either R or K, positively charged residues or D or E, negatively charged residues Thus, also encompassed in the present disclosure are the peptides having a formula III-I, wherein the first amino acid residue is positively charged R or K. or negatively charged D or E.

In one embodiment, the present disclosure is related to an isolated polypeptide having an amino acid sequence set forth in SEQ ID NO: 15-20, 22, 24-27, 30-37, 42-64, 67 and 68, wherein the first amino acid (the amino acid at the N-term) is substituted with a lysine residue, the first amino acid of SEQ ID NO: 21 is substituted with an arginine, and the first amino acid of SEQ ID NO: 29 is substituted with an aspartic acid.

In still other embodiment, the present disclosure is related to an isolated polypeptide having an amino acid sequence set forth in SEQ ID NO: 15-22, 24-27, 30-37, 42-64, 67 and 68, wherein the first amino acid of SEQ ID NO: 15-22, 24-27, 30-37, 42-64, 67 and 68 is substituted with an aspartic acid or a glutamic acid residue, and the first amino acid of SEQ ID NO: 29 is substituted with a lysine or arginine residue.

In still other embodiment, the present disclosure is related to an isolated polypeptide having an amino acid sequence set forth in SEQ ID NO: 15-22, 24-27, 30-37, 42-64, 67 and 68, wherein the amino acid sequence of SEQ ID NO: 15-20, 22, 24-27, 30-37, 42-64, 67 or 68 further comprises up to 14 arginine residues at the N-terminus, the amino acid sequence of SEQ ID NO: 21 further comprises up to 14 lysine residues at the N-terminus, and the amino acid sequence of SEQ ID NO:29 further comprises up to 14 glutamic acid residues.

However, the polypeptides according to the present invention are not limited to the above-described sequences, but include biological equivalents thereof. The term biological equivalents refer to polypeptides which contain additional modifications to the amino acid sequences disclosed herein, but have substantially the same or similar activity as the polypeptide disclosed herein. Such modifications include, for example, a deletion, insertion and/or substitution of one or more residues in the amino acid sequence. The modifications may be determined in consideration of properties of the similarity of side chains such as sizes, charges, hydrophobic or hydrophilicity. Based on the characteristics of the side chains in terms of size, shape and chemical/electrical properties, it is considered that arginine, lysine and histidine are positively charged residue; alanine, glycine, and serine are having similar size of side chains; phenylalanine, tryptophan and tyrosine are having similar structure of side chains. Thus, in consideration of this, arginine, lysine and histidine; alanine, glycine and serine; phenylalanine, tryptophan and tyrosine are considered biologically equivalent.

Also when introducing modifications, hydrophobic indices may be considered. Each amino acids is endowed with a unique hydrophobic index according to its hydrophobicity and charges as follows: Isoleucine (+4.5); Valine (+4.2); Leucine (+3.8); Phenylalanine (+2.8); Cysteine/Cystine (+2.5); Methionine (+1.9); Alanine (+1.8); Glycine (−0.4); Threonine (−0.7); Serine (−0.8); Tryptophan (−0.9); Tyrosine (−1.3); Proline (−1.6); Histidine (−3.2); Glutamate (−3.5); Glutamine (−3.5); Aspartate (−3.5); Asparagine (−3.5); Lysine (−3.9); and Arginine (−4.5).

The hydrophobic indices described as above are useful in imparting proteins with an interactive biological function. It is known that similar biological activities are obtained from substitutions with amino acid having similar hydrophobic index. When modifications are performed in reference to the hydrophobic index, it is preferable to select an amino acid for a substitution having a hydrophobic index difference within ±2, more preferably ±1, particularly more preferably ±0.5.

Also it is known that the substitutions between amino acids having similar hydrophilicity value result in biologically equivalent proteins.

For example, U.S. Pat. No. 4,554,101 may be referred, in which hydrophilic values are disclosed as follows: Arginine (+3.0); Lysine (+3.0); Aspartate (+3.0±1); Glutamate (+3.0±1); Serine (+0.3); Asparagine (+0.2); Glutamine (+0.2); Glycine (0); Threonine (−0.4); Proline (−0.5±1); Alanine (−0.5); Histidine (−0.5); Cysteine (−1.0); Methionine (−1.3); Valine (−1.5); Leucine (−1.8); Isoleucine (−1.8); Tyrosine (−2.3); Phenylalanine (−2.5); Tryptophan (−3.4).

Further, for amino acid substitutions that fall within the scope that does not result in a substantial change in the biological characteristics compared to a parent protein, H. Neurath, R. L. Hill, The Proteins, 3rd Edition, Academic Press, New York, 1979 may be referred. For example, typical substitutions include Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu and Asp/Gly.

Furthermore, when considering variants having biologically equivalent activities as described above, it is encompassed in the present invention not only the amino acid sequences disclosed herein or nucleic acids encoding the same as described below, also the sequences substantially identical to the sequences disclosed herein. The term "sequences substantially identical" refers to those showing preferably at least 61%, more preferably at least 70%, still more preferably at least 80%, most preferably at least 90% similarity to the sequence disclosed herein, when aligning sequences with the sequence disclosed herein so as to correspond to each other to the highest possible extent and analyzing the aligned sequences using algorithms that are generally used in the art. Methods of alignment of sequences for comparison are well-known in the art. Various programs and alignment algorithms are described in, for example, Smith and Waterman, *Adv. Appl. Math.* (1981) 2:482; Needleman and Wunsch, *J. Mol. Bio.* (1970) 48:443; Pearson and Lipman, *Methods in Mol. Biol.* (1988) 24: 307-31; Higgins and Sharp, Gene (1988) 73:237-44; Higgins and Sharp, *CABIOS* (1989) 5:151-3; Corpet et al., *Nuc. Acids Res.* (1988) 16:10881-90; Huang et al., *Comp. Appl. BioSci.* (1992) 8:155-65 and Pearson et al., *Meth. Mol. Biol.* (1994) 24:307-31. The NCBI Basic Local Alignment Search Tool (BLAST) (Altschul et al., *J. Mol. Biol.* (1990) 215:403-10) is available from the NBCI and the like, for use in connection with the sequence analysis programs such as blast, blastp, blasm, blastx, tblastn and tblastx. The BLAST can be accessed at http://www.ncbi.nlm.nih.gov/BLAST/. A description of how to determine sequence identity using this program is available at http://www.ncbi.nlm.nih.gov/BLAST/blast_help.html.

In one embodiment, the C- and/or N-term, particularly C-term may be substituted with an inert or non-reactive group such as $NH_2$ group to increase the stability of the peptides.

In a further aspect, the present disclosure relates to nucleotides encoding the peptides disclosed herein and vectors containing the same and cells transformed/transfected with the vector. One of ordinary skill in the art would be able to select appropriate vectors and cells to which the present nucleotides are cloned and delivered, respectively. One of ordinary skill in the art would be able to determine the nucleotides sequences encoding the present peptides without undue experimentation based on the known codon table and codon degeneracy and codon preferences. For example nucleotide sequences encoding SEQ ID NO: 1 and 17 peptides may be represented by CARYUNGUNGU-NAAR; and MNGCARYUNGUNGUNAARU-UYMNGGCNYUNCCNUGY, respectively in which R=A, G; K=G,T; H=A,C,T; D=A,G,T Y=C,T; S=C,G; B=C,G,T; N=A,G,C,T; M=A,C; W=A,T; V=A,C,G.

The present peptides as disclosed herein can be attached or used to attach various materials of biological or non-biological origins or the surfaces thereof. Thus such properties may be used for mediating attachment among the same or different materials. For example, the present peptide may be used for attaching cells to culture plates, or for attaching among cells, or the present peptides conjugated to a label such as fluorescent dye may be used for labeling cells or tissues. Also the present peptides conjugated to a therapeutic agent such as bone morphogenic proteins and the like may be used to increase the therapeutic effects of the agent when the tissues of interest are treated therewith.

Without being intended to be limited by this theory, the present peptides is found to increase the adhesiveness by having affinity to the peptidoglycan layers, and further to the components (lipopolysaccharide are included) of the cell walls of microorganisms as well as to (1,3)-betaglucan a component of yeast cell wall. Thus the present peptides can have wide applications in various fields.

Also the present peptide can be connected to various compounds via epsilon amino groups and used for delivering the compounds.

Without being intended to be limited by this theory, the present peptides exhibit excellent affinity to proteoglycans, a component of cartilage. Thus the present peptides can be used advantageously in the field of tissue regeneration and also plastic surgery. Thus, the present peptides may find applications in cartilage regeneration and the like. The material which may be used with the present peptides includes materials, particularly biological material classified as biological materials such as animal, plant and any part therefrom, including for example, cells, tissues, and organs or the surfaces thereof.

In this perspective, the present peptides may further comprise targeting or labeling agents.

In other aspect, the present disclosure relates to a bioconjugation composition comprising the present peptide disclosed herein In still other aspect, the present disclosure relates to an adhesive composition for biological or non-biological material.

In one embodiment, the present peptides or compositions comprising the same are applied to cells for attachment including cells from plants, insects and animals. For example, the present peptides may be used for attaching multipotent cells, adult stem cells, and precursor cells. The examples of pluripotent cells include ES cells, GS cells, and iPS (induced pluripotent stem cells). The examples of adult stem cells includes MSC (mesenchymal stem cells), Hematopoietic stem cells, and nerve stem cells. The examples of precursor cells include cells from skin, dermis, endothelium, epidermis, muscle, myocardium, nerve, bone, cartilage, brain, epithelium, heart, kidney, pancreas, spleen, oral cavity, cornea or hair.

The examples of cells from human includes but are not limited to ES cells, iPS cells, MSC, chondrocytes, osteoblasts, osteoclasts, mesenchymal cells, myocytes, myocardial cells, nerve cells, hepatocytes, embryonic cells, fibroblasts, corneal epithelial cells, corneal endothelial cells, vascular endothelial cells and hematopoietic cells. The cells may be autologous or heterologous.

The surfaces onto which the present peptides or compositions are applied are not particularly limited, and include organic or inorganic surfaces of hydrophilic or hydrophobic properties. In one embodiment, the present peptides or compositions may be applied to surfaces of biological origin or non-biological origin such as plastics, glasses, high molecular weight synthetic resins and metals.

The use of the present peptides or compositions includes but is not limited to (1) adhesion between substrates in water (water or saline water); (2) orthopedic treatments such as bones, ligaments, tendons, meniscus and muscle treatment and artificial material implants; (3) treatment such as perforation, fissure, incision, or ophthalmic adhesions such as corneal transplantation, and artificial cornea insertion; (4) dental applications such as braces, machining dentures, crown mounting, teeth fixation, broken tooth treatment, and filler fixation; (5) surgical treatment such as vascular occlusion, cell tissue grafting, artificial material grafting, wound closure; (6) adhesions in plants such as plant graft, wound healing; (7) a cell or tissue culture comprising stem cells; (8) substrate materials for medical devices such as artificial organs, denial, surgical or ophthalmic devices, such as implants, bone removers, bone cages, guide wires, catheters and stents; (9) adhesion of hone, titanium or ceramic and the like; and (10) a biocortjugation of various biomaterials including bioactive agents, labeling agents and target materials.

In one embodiment, the present peptides or compositions may be used in dental, ophthalmic or orthopedic treatment for cell or tissue graft or regeneration, in which case the surface on which the present peptide or compositions may be applied include but is not limited to PLGA, hydroxyapatite, zirconium, titanium, iron, stainless steel, titanium, platinum, gold, and alloy.

In still other embodiment, the present peptides or compositions may be used supports for attaching cells to supports. The supports include but are not limited to cell culture plate, microbeads, substrate, tissue implants and the like. The present peptides or compositions may be used for cell or tissue cultures, particularly for stem cell cultures. According to one embodiment of the present disclosure, the present peptides are found to be very effective in attaching cells in comparison to currently used agents used for cell adhesion (refer to FIGS. 1, 2, 3, 4, 5 and 6 and the like).

In still other embodiment, the present peptides or compositions may be used for bioconjugation. The bioconjugation means chemical methods/means connecting two biological molecules via stable covalent bonds. The present peptides may be conjugated directly or via a small molecular weight linker to various biomolecules such as proteins, nucleic acids, lipids, or carbohydrates including enzymes or hormones. The bioconjugation may be used as a research tool for detecting or monitoring biochemical materials, or for conjugation of a therapeutic agent for targeted therapy or improving the efficacy of the agent. In one embodiment, the present peptides are used for conjugating bone morphogenic protein to increase the therapeutic efficacy the protein.

The present peptides or compositions may be used in manner as generally known in the art. And the typical method is to apply the present peptides or composition to the surfaces. For example, commercial products such as Cell-Tak® (BD Biosciences, USA) may be referred for formulations, amount of use, usages.

The composition comprising the present peptides may be prepared in solvent type, water-soluble type or solvent free type and may be used in the amount of 0.1 to 1000 ng/mm$^2$, particularly 1 to 100 ng/mm$^2$ based on the area of the surfaces to be treated without being limited thereto.

The amount of the present compositions to be applied or the adhesiveness of the composition may be determined or controlled by treatment with surfactants, oxidizing agents, crosslinking agents, or fillers or by adjusting the concentration of the present peptides. For example the fillers may include but are not limited to collagen, hyaluronic acid, chondroitin sulfate, elastin, laminin, casein, hydroxyapatite, albumin, or fibronectin.

Hereinafter, the present invention will be described in further detail with reference to examples. It is to be understood, however, that these examples are for illustrative purposes only and are not intended to limit the scope of the present invention.

EXAMPLES

Example 1

Preparation of the Present Peptides

The peptides used in the Examples were synthesized by 9-fluorenylmethyloxycarbonyl (Fmoc) method (Lugen Sci, Korea; Peptron, Korea). To confirm the reproducibility of the experimental results using the peptides, identical sets of peptides were independently synthesized 2 or 3 times from Lugen Sci and Peptron, respectively. Consistent results were obtained from the peptides synthesized from different companies and among different batches.

Example 2

Analysis of the Present Peptide for Conjugating Fluorescent Materials and for Adhesiveness thereof to Various Non-biological Origin Surfaces One of the peptides synthesized in Example 1, A7-1 (RQLVVKFRALPC; SEQ ID NO: 17)(corresponding to 12mer (A) of Table 1) was conjugated to a biotin (Thermo Scientific, USA) or a FITC (Sigma, USA) to a cysteine residue via —SH group, which were then used to treat a glass., PCL, Ti, Col, Zr, vinyl, and PS fiber (concentration 10 µM in PBS, adsorption for 20 min at RT followed by washing one with PBS). The adsorption was analyzed by a FITC fluorescent image analyzer LAS (Fuji, Japan). To liberate the biotin from the peptides, the conjugated peptides were treated with DTT (100 mM in PBS, 20 min at RT followed by washing one time with PBS). As a control, dyes were used alone.

Results are in FIGS. 1A to 1D. As shown there, it was found that the biotins are strongly attached through the present peptide to the surface of the material employed. Particularly the attachment was disappeared by treating the surface with DTT (FIG. 1A). This confirms that the biotin and FITC were attached to the surfaces through the present peptide.

Example 3

Analysis of the Present Peptide for the Adhesiveness to Various Materials of Biological or Non-biological Origin Experiments basically the same as Example 1 were performed except that Bio-OSS® (Geistlich Pharma, Inc) and MBCP™ (Biomatlante), a widely used bone graft, were used instead of the glass. The conditions were as follows: Bio-OSS® particles were reacted with 10 µM of the present peptide conjugated with FITC for 10 min at RT, which was then washed 5 times for 48 hrs in PBS containing 0.05% TWEEN®-20 and analyzed by a confocal microscope (Zeiss LSM-700 model with Zen 2011 software, x20).

Also, to confirm the adhesiveness of the present peptide in in-vivo environment, the present peptides were injected into various tissues and the thin sections were prepared from the tissues for analysis. Specifically, 10-20 µl of A7-1 of the present peptide not conjugated or conjugated with Cys or FITC dye, or Cys or FITC dye alone at the concentration of 10 µM dissolved in PBS were administered to various tissues by injection or local application. Two hours after the administration, the mice were sacrificed and the tissues were harvested. The tissues were then washed three times in PBS for 30 min and thin sections were prepared therefrom and analyzed by a confocal microscope. The tissues used in the experiment were cartilage, skin, hair, subcutaneous fat and eye ball. In the case of cartilage, the tissue was partially treated with collagenase to expose elastic fibers followed by extensive washing.

Results are shown in FIGS. 2A to 2M, which indicate that the present peptides are able to attach to various materials from biological and non-biological origin. The results show that the present peptide has an excellent adhesiveness to a commercial bone graft, particularly tissues containing large amount of proteoglycan such as elastic tissues and connective tissues, and tissues containing large amount of collagen or hyaluronan, and cell walls of yeast and bacteria.

Figure 4A:
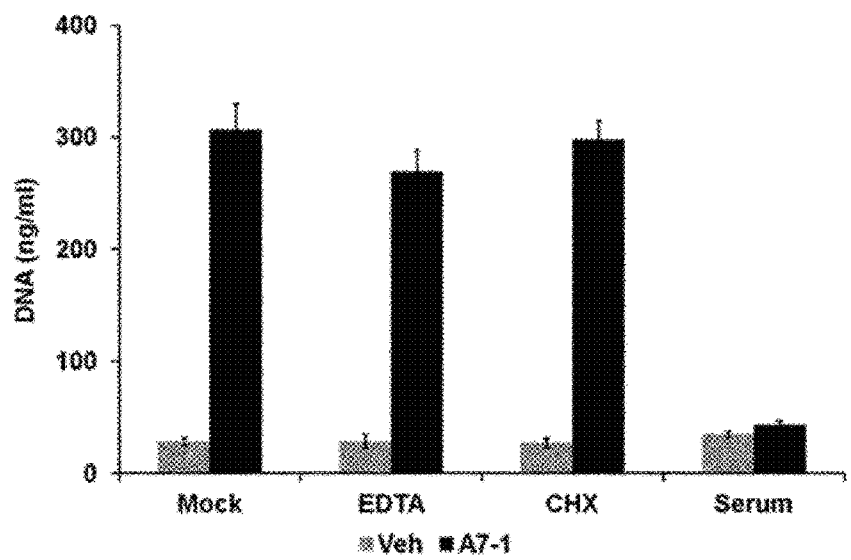
FIGS. 4A to 4C show the analysis results of possible mechanism of the present peptide to increase the adhusiveness of cells.
Figure 4B:
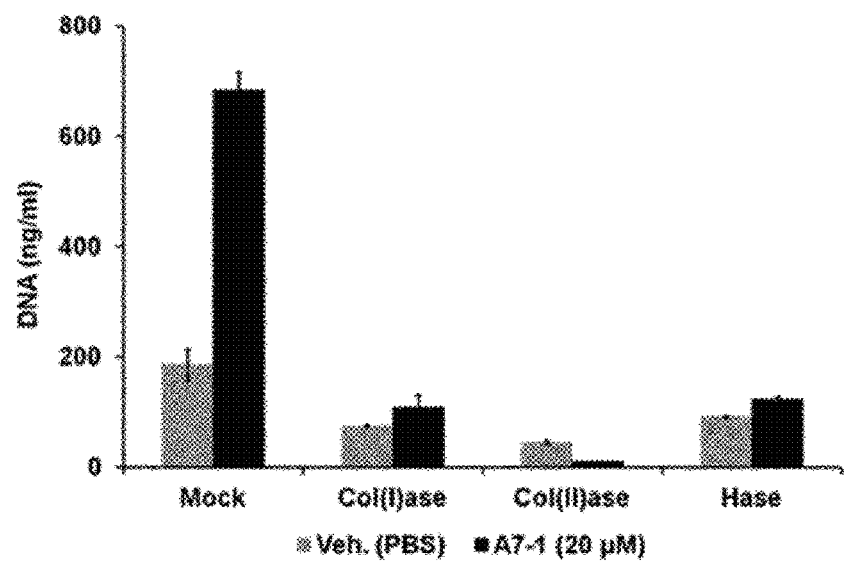
Figure 4B:
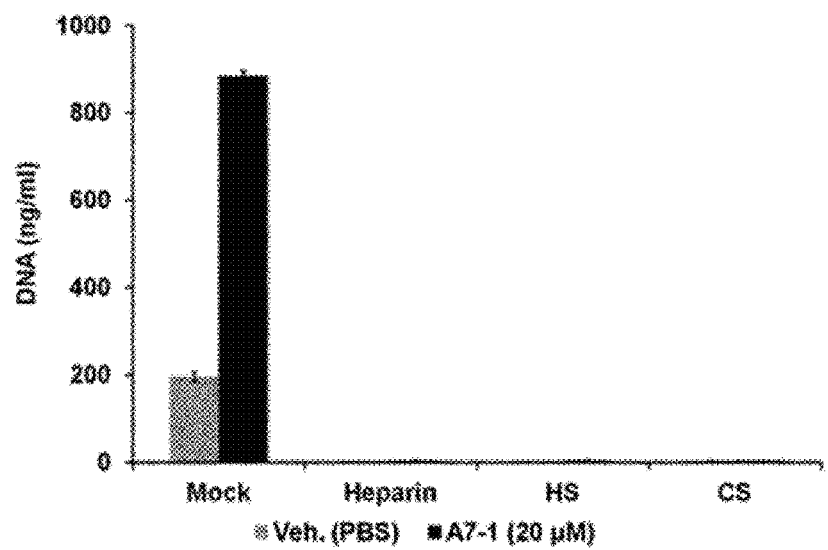

Also the present peptide shows an excellent adhesiveness to cartilage tissues (*) which are abundant in GAG (glycosaminoglycan) such as heparan sulfate, heparin, chondroitin sulfate, which corresponds to the result of FIG. 4B. Meanwhile, GAG includes four types of materials, hyaluronic acid, dermatan sulfate, chondroitin sulfate, heparin and heparan sulfates, and keratan sulfate. All of them are essentially consist of a glucose bonded to amine group or a galactose, N-acetylglucosamine or N-acetylgalactosamine and the like. The results found in the present disclosure suggest that the present peptides have an affinity to a hexose and thus are able to function in a target specific way.

Example 4

Improvement of Cell Attachment by the Present Peptides

Materials used in the present Example are as follows: 10 mM peptide solution in PBS (Stock solution); plastic hydrophobic cell culture plate of 35 mm in diameter (for cell culture, Corning); DMEM(Dulbecco Modified Eagle Medium, cell culture medium: Hyclone); Fetal bovine serum (Hyclone); and C2C12 (mouse myoblast, cell, ATCC, CRL-1772); MC3T3-E1 (Mouse C57BL/6 calvaria cell, ATCC, CRL-2593) and ST2 (bone marrow-derived stroma cell: EMBO J. 7:1337?1343, 1983); STO (feeder cell: ATCC, CRL-1503), HEK-293 (ATCC, CRL-1573), SaOS2 (ATCC, HTB-85), HeLa(ATCC, CCL-2), ROS17/2.8, NIH3T3 (ATCC, CRL-1658), RAW264.7 (ATCC, TIB-71), hMSC (Lonza, PT-2501), hPDL(HPLF) (Sciencell, Cat.#2630), hDPSC (isolated from human tissue according to Cells Tissues Organs 184: 105-16), mBMSC (Primary Bone Marrow Stromal Cell from mouse), MC (Primary Mouse Calvaria cell), MEF (Mouse Embryonic Fibroblast)

Experiments were done as described below.

The effect of the present peptide on the cell attachments was examined either by using a culture plate pre-coated with the present peptide or by adding the present peptide directly to a medium. Both methods produced the same results. For preparing the plates pre-coated with the present peptide, the present peptide was added to PBS or cell medium without FBS, which was then used to coat culture plates for 30 min and removed. Then cells were added thereto and the cells' attachment to the plates were measured for various times. Also for testing the present peptide by adding directly in medium, the present peptide was added when cells were suspended in the medium just before adding them to the plates. The cell attachments were measured as described below. Cells not treated with the present peptide were used as a negative control. And cells cultured in the plates treated with PBS or poly-L-lysin were used as a positive control. Cells were then examined by optical microscopy or confocal microcopy for overall examination of the cells, actin filament structure of the cells and irregularity of marginal shape of the cell membrane, for which the cells were stained for F-actin. Further to quantify the attachment, DNA amount of cell's metabolism were measured. The metabolism was determined by measuring absorbance using CK-8 (Dojindo), and DNA amount was determined by measuring fluorescence using Picogreen assay kit (Life Technologies) according to the manufacturer's instruction. To only use the cells attached for DNA amount and cell metabolism, the cells which were not attached were discarded by washing 2 times with PBS Results are shown in FIG. 3A to 3F. As shown there, the present peptide is able to increase the attachment of various types of anchorage dependent cells from primary cells, established cells, freeze and thawed cells and feeder cells, and shows a superior effect compared to PLL a material previously used for cell attachment.

Example 5

Identification of Mechanism of the Present Adhesive Peptide

The following experiments were done to identify the mechanism of the adhesiveness of the present peptide.

(1) Determination of the Requirement of Protein Synthesis

Firstly, Cells were treated with EDTA or cyclohexamide (CHX) known to prevent the protein synthesis (10 µM, 37° C. for 1 hr) or GAC as described above and tested for the adhesiveness.

Results are shown in FIG. 4A. From the figures, it is observed that EDTA or CHX does not affect the adhesiveness of the cells. Namely, it can be suggested that the adhesiveness exhibited by A7-1 of the present peptide does not requires the presence of electrolytes (result from EDTA) on the cell surface or new protein synthesis (result from CHX). One the other hand, it is observed that the serum inhibits the adhesiveness of the cells at early stage, which can be attributed to the binding of various types of GAG abundantly present in the serum to the present peptide. The change in the concentration of GAG present in the serum is known to be associated with development of various diseases (Volpi N. et al., Biochim Biophys Acta. (1995) Vol. 18: 49-58; Komosinska-Vassev K. et al., Clin Chim Acta. (2003) Vol. 331: 97-102; Anttonen A. et al., Lung Cancer. (2003) Vol. 41: 171-7; Fuster M. M. et al., Nat Rev Cancer. (2005) Vol. 5: 526-42; Hong Lu et al., 2010. Glycobiol. Insights Vol. 2: 13-28; Anower-E-Khuda M. F. et al., Glycobiology. (2013) Vol. 23: 865-76; Ibrahim S. A. et al., J. of Medical Lab. & Diagnosis (2013) Vol. 4: 8-20). Accordingly, this indicates that the present peptides can be used advantageously as an agent for regulating concentration of GAG in blood or an agent to targeting GAG. Also the results show that the present peptides exhibit its function of improving the adhesiveness of the cells not through the interaction with proteins in the cell membrane.

(2) Determination of the Involvement of Non-proteinous Material

In this experiments, the involvement of non-proteinous material was determined. For this, the involvement of proteoglycans which are contained in ECM (Extracellular Matrix) in large amount were tested.

The Molecular Affinity of the Present Peptide to Proteoglycan

GAGs (glycosaminoglycan) such as heparan sulfate, heparin, chondroitin sulfate, dermatan sulfate, keratan sulfate and the like, the major components of proteoglycan, are main components of ECM and help maintaining the morphology of cells by maintaining the structural integrity of ECM. Further they are known to regulate the cells' adhesiveness and polarity. Such functions exhibited by ECM help the cells to adapt to the environment as well as regulate the physiology of the cells because of their direct involvement in a series of complex metabolism in the cells. The affinity of the present peptides to proteoglycans were tested by the following three experiments: (i) affinity chromatography; (ii) cell attachment analysis through competitive binding assay using purified GAG; (iii) analysis of inhibition of cell attachment by enzymes specifically breaking down ECM comprising GAG components. In the case of enzyme treatment, hyaluronidase(Sigma) and Collagenase (Sigma) were used. As purified GAGs, yaluronan (Sigma), chondroitin sulfate (Sigma), heparin (Sigma), heparin sulfate (Sigma) were used.

(i) Analysis of the interaction of the present peptide-haparin, or peptide-N-acetylglucosamin (GlcNAc) by affinity chromatography For chromatography, heparin-agarose beads (Biovision) and GlcNAc-agarose beads (Sigma) were used. 10 ng of FITC labelled peptide (F-peptide) was mixed om PBS-T buffer with heparin-agarose beads and GlcNAc-agarose beads, each precoated with BSA, and incubated at RT for 10 min. Then the mixture was washed 3 times with PBS-T buffer and resuspended in PBS for fluorescent measurement. For competitive binding experiments, the present peptide not labelled with FITC (Cold) was added to the mixture at various ratios of 1:1, 1:10 (10 times) and 1:100 (100 times) and allowed for incubation followed by fluorescent measurement. As a negative control, only FITC dyes were used to react with the beads. Further fluorescent signals from a sample containing just beads suspended in PBS were used as a blank. The results of FIG. 4B show that the present peptide has a strong affinity to heparin and GlcNAc, a component of GAG.

(ii) Analysis of the effect of GAG on the cell adhesiveness by competitive binding using purified GAG.

The results of FIG. 4B shows the inhibition of the adhesiveness of the present peptide by treatment with GAGs in a competitive manner indicating that the adhesiveness of the present peptides are inhibited by the addition of heparin, heparan sulfate, or chondroitin sulfate.

(iii) Inhibition of the improvement of the adhesiveness exhibited by the present peptide by use of enzymes specifically digesting ECM which contains GAG: Not only proteoglycans constituting ECM but also fibril proteins including collagen and the like all include GAGs as one of their components. When collagens comprising GAGs were hydrolyzed by use of collagenase, or hyaluronidases were used to hydrolyze hyaluronans, it is found that they all inhibit the adhesiveness of the present peptide. This also indicates that the cell adhesiveness exhibited by the present peptide is correlated with GAG Experiments were done as follows: (i) for competitive inhibition by treatment with purified GAG, GAG was added to cell suspension treated with trypsin at the concentration of 5 mg/ml and incubated at 37° C. for 10 min, which was then transferred to a culture dish coated with the present peptide and incubated for 30 min. After that, the amount of DNA contained in the attached cells was quantified to measure the adhesiveness. The quantification of DNA was performed by picogreen assay kit (Life Technologies); (ii) for assaying the effect of collagenase and hyaluronidase on the adhesiveness, cells treated with trypsin were suspended in a medium not containing fetal bovine serum and the enzymes were added thereto followed by incubation at 37° C. for 30 min. The enzymes were used at the concentration of 10,000 unit/$10^3$ cells. After the incubation with the enzyme, the enzymes were inactivated by adding EDTA and FBS. The cells were then centrifuged and resuspended in a fresh medium and incubated for 2 hrs. The attached cells were washed 2 times with PBS and harvested for DNA quantification by picogreen assay.

Results are shown in FIG. 4B. From the figure, it is observed that the present peptide has a strong affinity to proteoglycans, which is a major component of cartilage tissue, indicating that the present peptide can be used advantageously for tissue regeneration, and for clinical application in the field of plastic surgery and the like. Thus the excellent affinity to proteoglycan layers of the tissues such as cartilages indicates the usefulness of the present peptide for tissue regeneration and drug delivery.

(3) Comparative Experiment with RGDS

The present peptide A7-1(10 μM) or A7-1 together with soluble RGDS peptide (0, 10, 100 and 1000 μM) for competition assay were added to anchorage dependent cells MC3T3-E1 in a test tube and incubated for 10 min. Then the cells were transferred to a culture plate and incubated for 10 min in a thermostatic incubator to allow the cells to attach. After 10 min, the medium was removed and the cells were washed 2 times with PBS to remove any unattached cells and a fresh medium without the peptide and CCK-8 (Dojindo) were added to the cells and incubated for 1 hr in a thermostatic incubator. Then the absorbance was measured at 450 nm. The medium mixed with CCK-8 only was used as a blank.

Figure 4C:
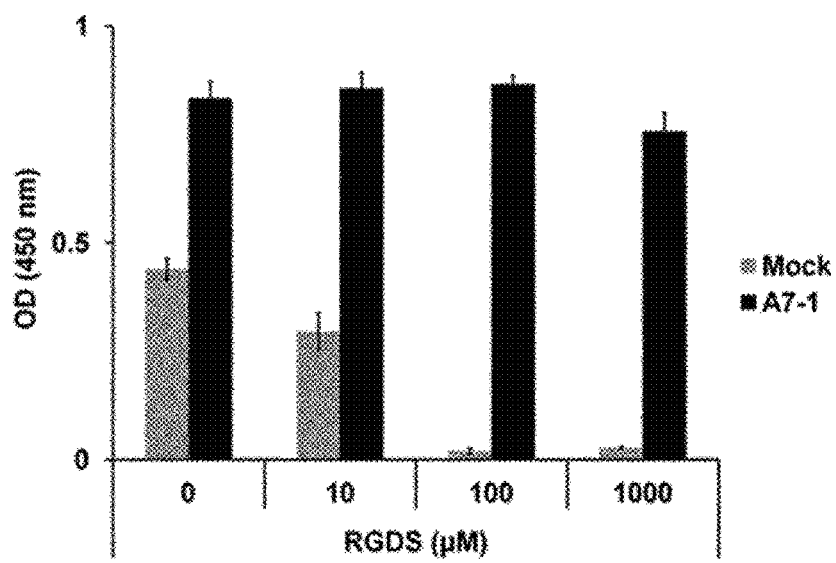

Results are shown in FIG. 4C. From the figure, when RGDS peptides are used alone, it is observed that the adhesiveness of the cells is decreased in a concentration dependent manner. In contrast, when the A7-1 and RGD peptide are used competitively, it is observed that the soluble RGD significantly decreases the adhesiveness of the cells to the bottom (substrate) by binding to integrin in the group not treated with A7-1. In the A7-1 treated group, it is observed that the adhesiveness of the cells is not affected at all. This indicates that the present peptide increases adhesiveness of cells by a mechanism different from that of RGD, in which RGD promotes the attachment of anchorage dependent cells through an interaction with integrin.

The results suggest that the present peptides have characteristics distinctive from RGD, the use of which are well established in the field of cell attachment and tissue regeneration, but the effective of which are known to be not good. Thus the present peptides can be advantageously used substituting RGDs.

Example 6

Improvement of Embryonic Stem Cells Using the Present Peptides

The present peptides were used to coat the culture plate or prepare nanostructure at the concentration level of 100 μM to investigate the attachment and pluripotency of induced pluripotent stem cells and human embryonic stem cells.

Human embryonic stem cells were cultured in hESC-media (with composition generally used in the related field), mTeSR (hES specific medium purchased from Stem cell technology), Essential 8 (hES specific medium purchased from Gibco BRL) and a medium only containing long/ml bFGF without any serum (to exclude the possible inhibition of the attachment of the cells by serum) to test the compatibility of the present peptide with various media currently used. Further the cells were analyzed by culturing cells in a colony state and by culturing cells in a single cell state by treating cells with 0.25% trypsin-EDTA. To test the effect of culturing ESC or iPSC in a feeder-free condition, Matrigel® (hESC) and gelatin (miPSC) were used as positive controls for comparison. The cells were also cultured in the presence of feeder cells as positive controls.

Figure 5A:
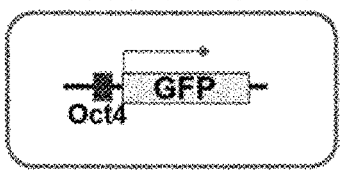
FIG. 5A is a schematic diagram of a reporter system and experimental process capable of testing the activity of Oct4, an indicator of sternness, to analyze the present peptide to promote the adhesiveness of iPSC (induced pluripotent stem cell)
Figure 5A:
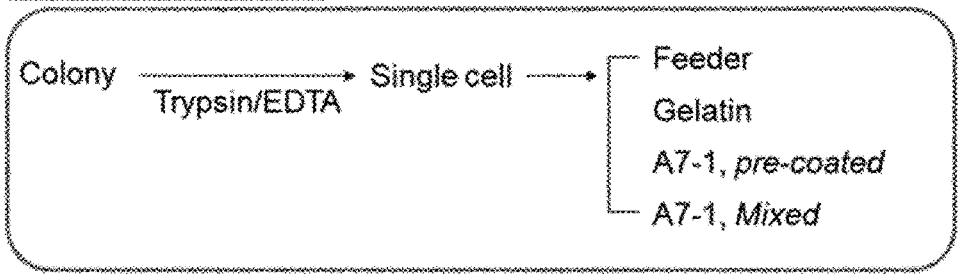
Figure 5B:
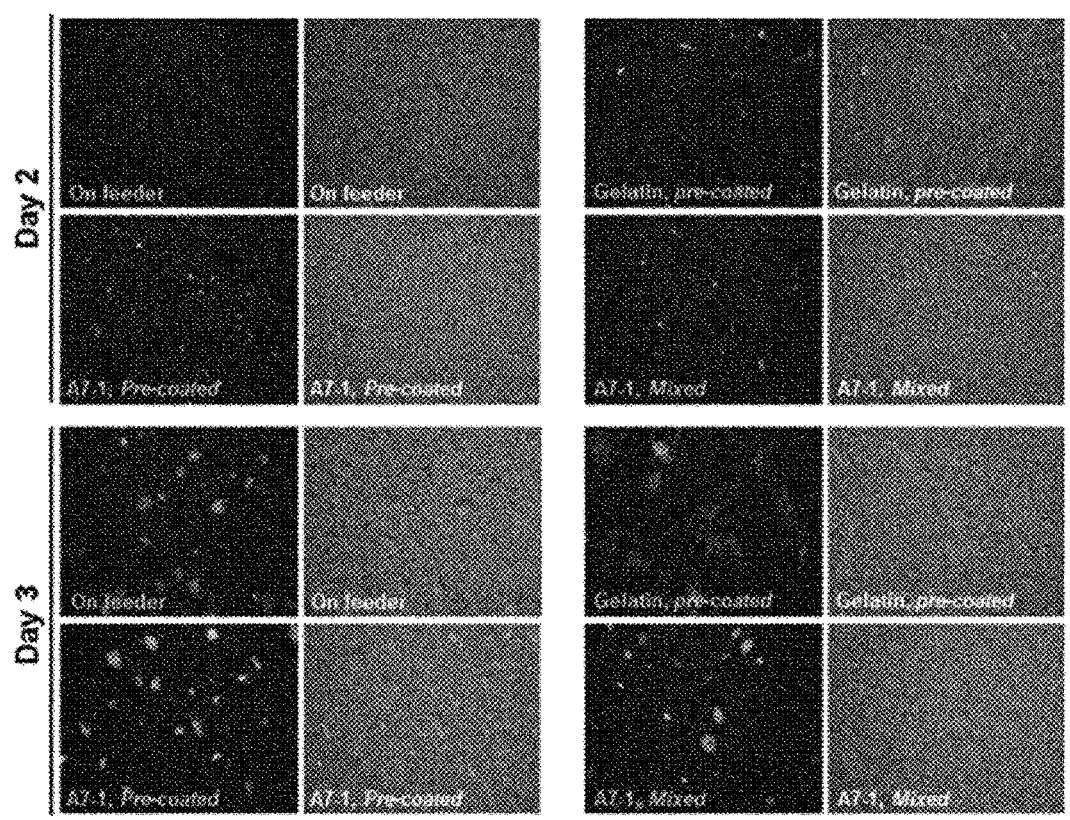
FIG. 5B is the results obtained using the system of FIG. 5A, in which the expression of Oct4 was examined at day 2 and 3 of the culture to analyze the sternness and adhesiveness of iPSC in the presence or absence of the present peptides. In the experiment, culture plates pre-coated with feeder cells or gelatin were used as controls and the present peptides were tested by pre-coating culture plates and adding or mixing the peptide in the cell medium. As a result, it is found that in the presence of the present peptides, the sternness and adhesiveness of iPSCs are well maintained in both tests of adding the peptides in the culture medium and pre-coating the plates.
Figure 5C:
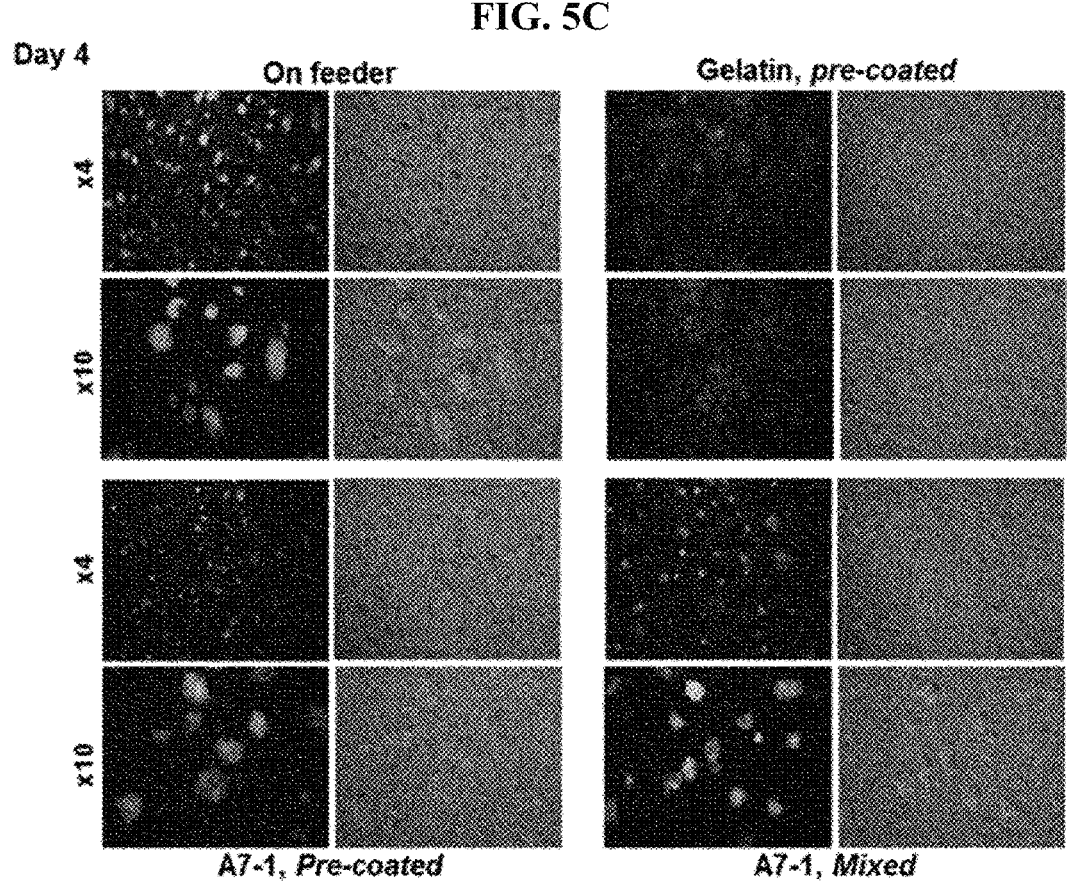
FIG. 5C is the same as FIG. 5B except that the cells were examined at day 4. The result indicates that the sternness and adhesiveness of iPSCs are well maintained in the presence of the present peptides.

The cells were analyzed by utilizing a plasmid (Szabo et al., 2002, Mechanisms of Development Vol. 115: 157-160) as shown in FIG. 5A able to detect the activity of Oct4 gene, a marker for sternness of embryonic stem cells (FIG. 5). Also other makers for sternness, the expression of Alp and Nanog genes were detected by staining with antibodies specific to each of the marker and examined by fluorescent microscope. Also the improvement of the cell attachment in hES cell culture was examined (FIG. 6).

Figure 6A:
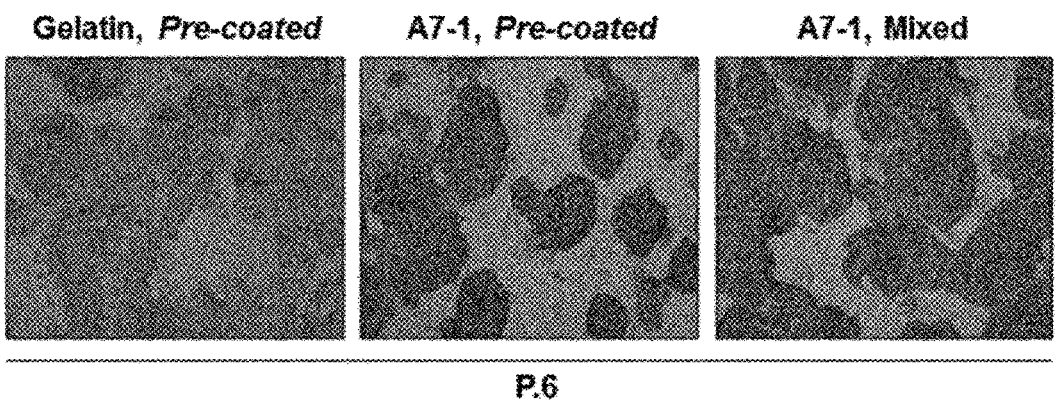
FIG. 6A is the results of experiments using Alp (alkaline phosphotase) as another sternness marker, which was analyzed by staining the cells for that marker. The results also indicate that the present peptides are able to mediate the adhesiveness of iPSCs and at the same time to maintain the sternness in both tests of pre-coating the plate and adding the peptide in the culture medium.
Figure 6B:
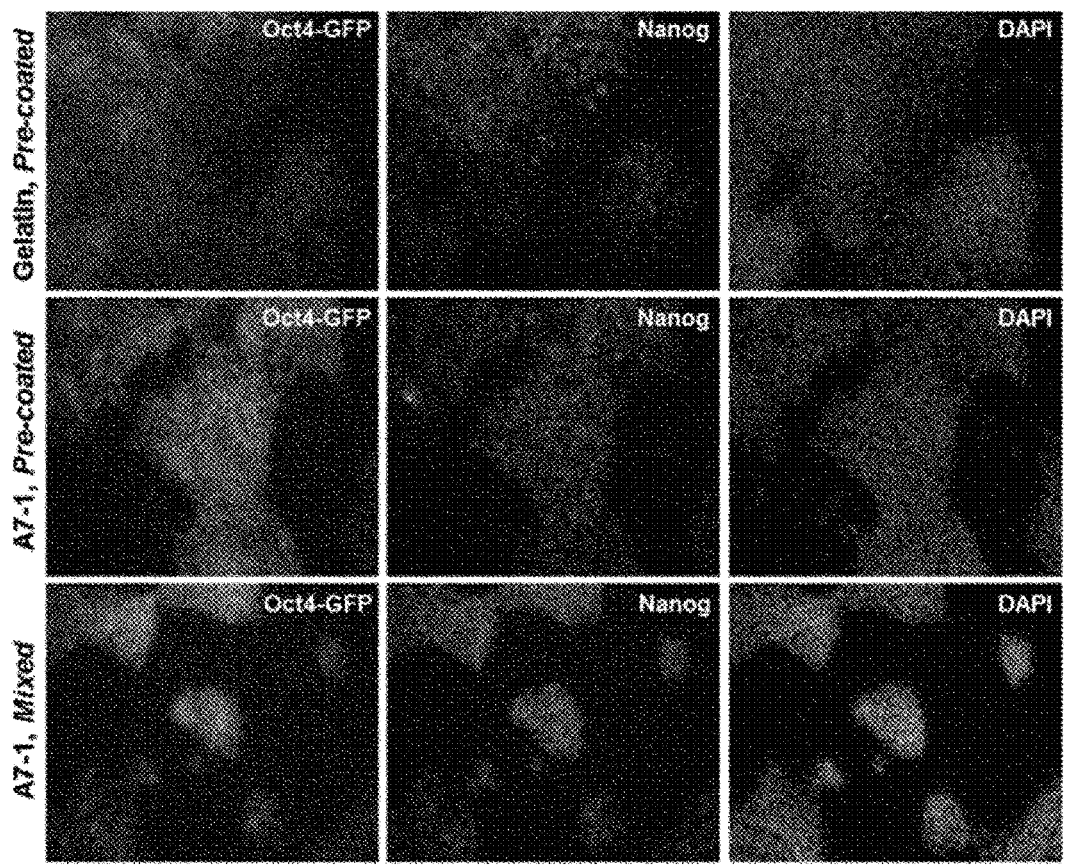
FIG. 6B is the results of experiments using Nanog as another sternness marker, which was analyzed by staining the cells for that marker. The results also indicate that the present peptides are able to mediate the adhesiveness of iPSCs and to maintain the sternness in both cases of pre-coating the plate and adding the peptide in a culture medium.
Figure 6C:
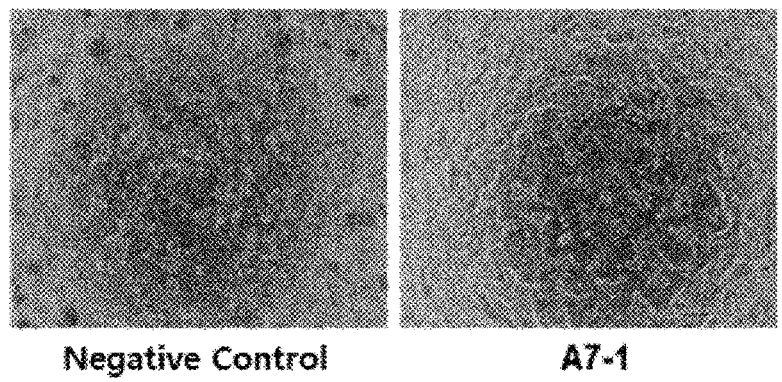
FIG. 6C is the same as FIG. 6A except that hESCs were used. The results indicate that the cells are able to proliferate well in the absence of feeder cells or Matrigel®.

Results are shown in FIGS. 5 and 6. From FIG. 5, it is observed that the present peptide is able to mediate the attachment of iPSC and maintain the stemness of the cells whether it is used to pre-coat the plate or is mixed in the medium (FIG. 5B). Further at day 4 of the culture, the effect of iPSC attachment and of maintenance of stemness is observed (FIG. 5C). Also as shown in FIGS. 6A and 6B by the expression of Oct4 and Nanog, the present peptides is able to mediate the attachment of iPSC and maintain the stemness of the cells whether it is used to pre-coat the plate or is mixed in the medium. The same results were obtained in the experiments using hESC in which the cells can grow by attachment and maintain the stemness by the present peptide and without the use of feeder cells or Matrigel® and the stemness (FIG. 6C).

Example 7

Bio-conjugation of the Present Peptide with a Protein

The following materials were used in the present Example: the present peptide synthesized as described in Example 1 was used at the concentration of 10 μM in PBS; plastic culture plate having an area of 1.9 cm² (24-well plate, Corning); DSS (Disuccinimidyl suberate, $C_{16}H_{20}N_2O_8$, Thermo Scientific Inc.); recombinant human BMP2 (rhBMP2, BD bioscience); DMSO (Dimethyl sulfoxide for dissolving DSS, Sigma-Aldrich); Tris-HCl, pH7.0 (Stop solution); PBS(phosphate buffered saline, reaction solution).

Figure 7A:
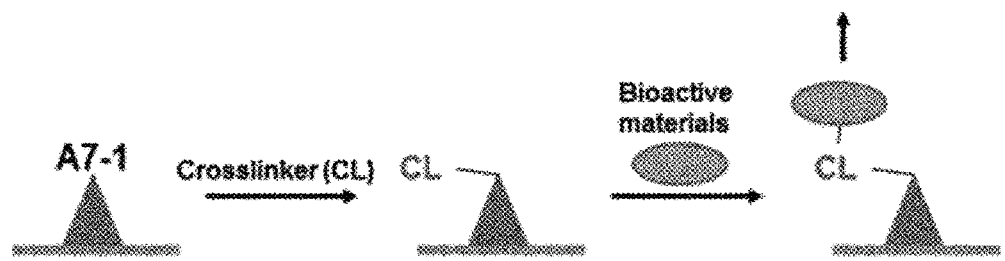
FIG. 7A is a schematic representation of a bio-conjugating process using the present peptides, in which the present peptide is conjugated to BMP2 via a linker, DSS (Disuccinimidyl suberate).

The schematic diagram explaining an analysis logic is shown in FIG. 7A. As shown in FIG. 7A, when the present peptide can be conjugated to a therapeutic protein with a desired activity such as BMP via cross linker, due to the adhesiveness of the present peptide, the local concentration of the therapeutic protein can be effectively increased and thus maximizing the therapeutic effect.

The experimental methods are as follows. Peptide-rhBMP2 covalent bond (Cross-linking) reaction was performed basically as described in the manufacturer's (Cross-linker) methods. Brief summarization is as follows: (i) peptide coating: 200 μl of the peptide solution (10 μM in PBS as prepared in Example 1) was dispensed into a cell culture plate and allowed to adsorb to the plate for 18 hrs at 4° C.; (ii) DSS-BMP2 complex formation: 20 molar excess of DDS relative to rhBMP2 was allowed to form covalent bonds in a total volume of 100 μl reaction solution for 1 hr. The concentration of rhBMP2 was used at the concentration of 300 ng per 1.9 cm². In this case, the culture plates coated with each of DSS, rhBMP2, and DSS-rhBMP2 were used as negative controls because it was observed that they were significantly removed during the washing step due their lack of adhesiveness to the surface of the plate; (iii) Peptide-DSS-BMP2 complex formation: 100 μl of DSS-BMP2 complex was carefully overlaid to a plated pre-coated with the present peptide and incubated at 4° C. for 24 hrs.; (iv) termination of the reaction: 200 μl of 1M Tris solution was added and incubated for 15 min at RT to neutralize all the DSS remaining after the covalent bond formation; (v) Washing step: washing 10 times with PBS, and DMEM without FBS was added and left at 37° C. before the cells were added; (vi) preparation of C2C12 suspension and differentiation into osteoblast: 4×10⁵ C2C12 cells were suspended in 300 μl of 2% FBS containing DMEM. DMEM in the plate pre-coated with peptide-DSS-BMP2 complex was removed and 300 μl of cell culture medium was added and incubated in 5% $CO_2$/37° C. incubator for 48 hrs to induce cell differentiation; (vii) Measurement of cell differentiation: the differentiation ability of C2C12 cells into osteoblast was examined by detecting the activity of Alkaline phosphatase by staining the cells.

Figure 7B:
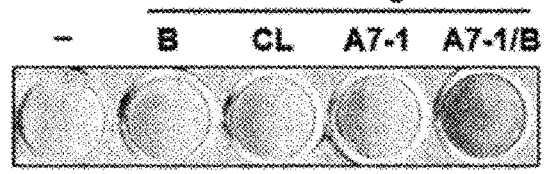
FIG. 7B is the results of testing the expression of Alp as a marker for bone differentiation in C2C12 cells at 48 hours after the C2C12 cells were treated with the present peptide by coating the culture plate with the present peptide. The results show that the expression of Alp is increased compared to BMP group (rhBMP2) or CL group (treated with cross-linker), which indicates that the present peptide is able to promotes a bone differentiation.
Figure 7B:

Results are shown in FIG. 7B. From the figure, it is observed that the Alp activity is significantly increased in comparison to the groups treated with BMP (rhBMP2) and with cross-linker (CL), respectively. This indicates the differentiation was promoted by the present peptide.

Example 8

Test of the Safety of the Present Peptide

Figure 8A:
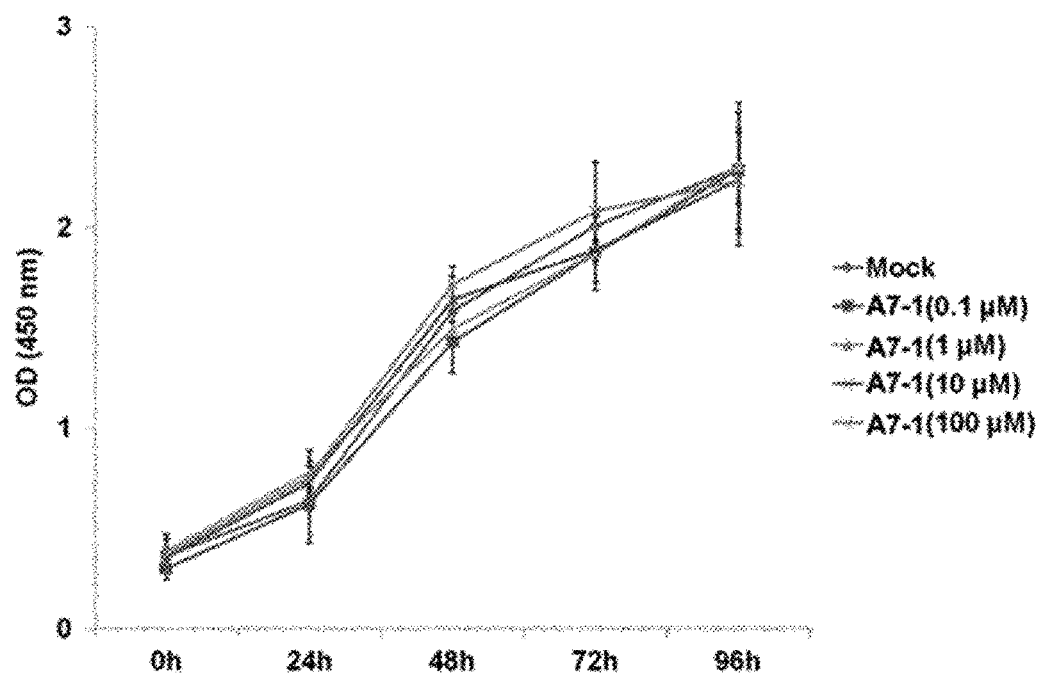
FIGS. 8A to 8C are results of testing the stability of the present peptides in osteoblast MC3T3-E1.
Figure 8B:
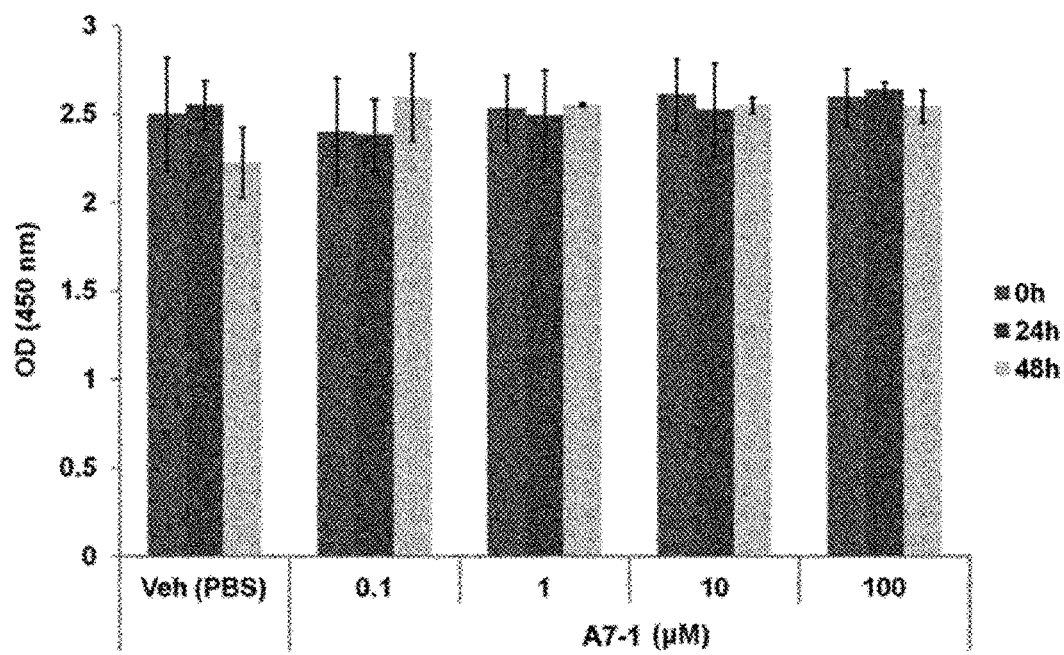
Figure 8C:
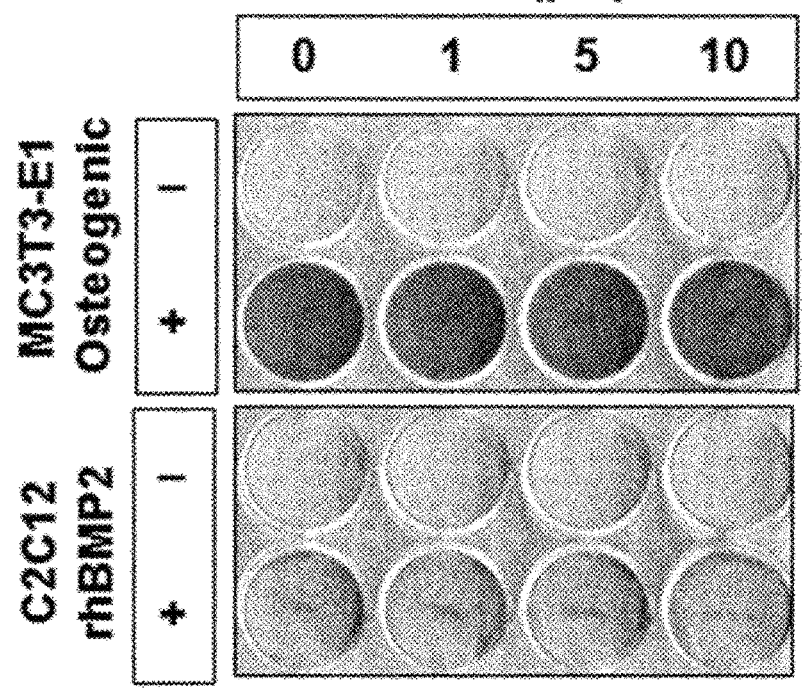

The safety of the present peptides was determined using osteoblast MC3TC-E1. Osteoblasts were treated with A7-1 peptide as prepared in Example 1 at the concentration of 0.1 μM, 1 μM, 10 μM and 100 μM. Then the effect of the present peptide on the proliferation (FIG. 8A), viability (FIG. 8B) and differentiation (FIG. 8C) on the cells was examined. For testing the effect on the proliferation, MC3T3-E1 and C2C12 cell lines were treated with BMP (rhBMP2, 10 ng/ml for 3 days) and differentiation medium for bone formation for 6 days to induce differentiation. The results were examined by cell staining. Results are shown in FIG. 8A to 8C. It is observed that the present peptide has no effect on the proliferation rate, viability rate or whether or not the cells are differentiated.

Figure 8D:
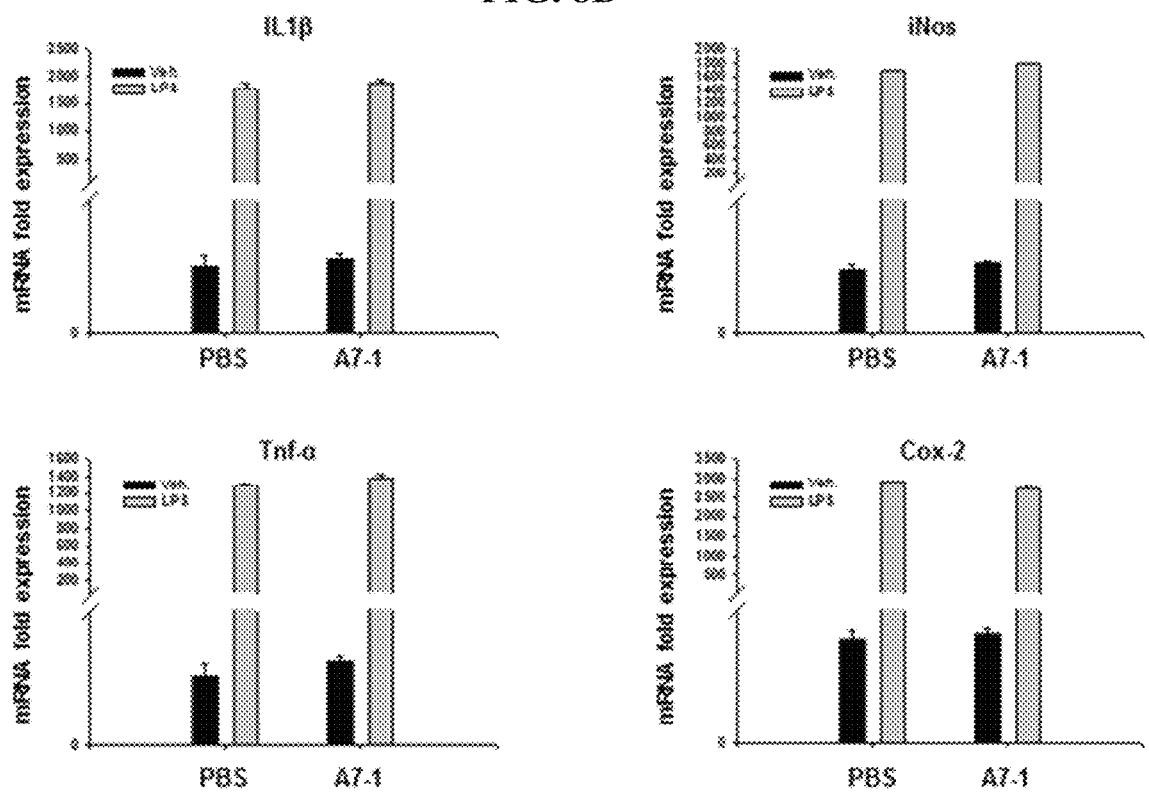
FIG. 8D is the results of testing the safety of the present peptides in monocytes isolated from mice, in which the monocytes were stimulated with the present peptides and examined for the induction of inflammation.

Also the safety of the present peptide was tested in mouse monocytes. The monocytes were isolated from bone marrow of mice and treated with the present peptide and examined for induction of inflammation. As a positive control, the cells were treated with LPS. At 24 hrs after the treatment, the cells were examined for the expression of inflammation markers IL-1β(interleukin-1β), Tnf-α(Tumor necrosis factor-α), iNos(Inducible nitric oxide synthase), Cox-2(cyclooxygenase-2) by quantitative real time reverse transcription PCR. The results are shown in FIG. 8D. From the figure, it is observed that the present peptides do not induce inflammation in cells and thus is confirmed as a safe material to be used in vivo.

Example 9

Testing the Improvement of Adhesiveness of the Primary Nerve Cell and Culture by the Present Peptide In the present Example, the effect of the present peptide on the attachment and culture of primary nerve cell in comparison to a currently used adhesive peptide. The peptide at the concentration of 100 μM was used to coat the culture plates or to prepare nanostructure to analyze the nerve cells obtained from the brain of mouse embryo and the spinal cord of mouse by optical microscope and determination of metabolism via CCK-8. As positive controls, Laminin and poly-L-ornithin (Sigma) were used for coating according to the manufacturer's instruction. To quantify the cell attachment at each of the hour indicated, the cells unattached were removed by washing with PBS, the mixture of cell medium and CCK-8 solution (Dojindo) was added to the cells and incubated for 1 hr followed by measuring the absorbance at 450 nm.

Figure 9A:
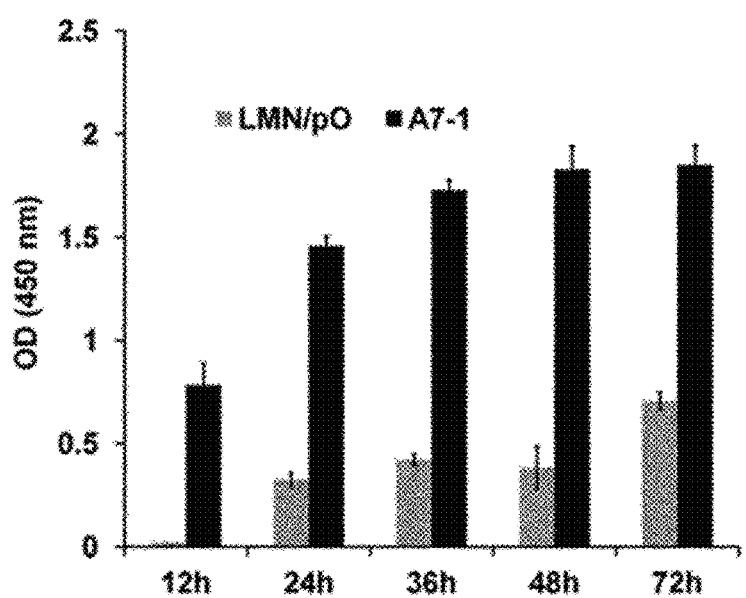
FIGS. 9A to 9C are the results of comparing the adhesiveness of the present peptide with that of previously known adhesive peptides.
Figure 9B:
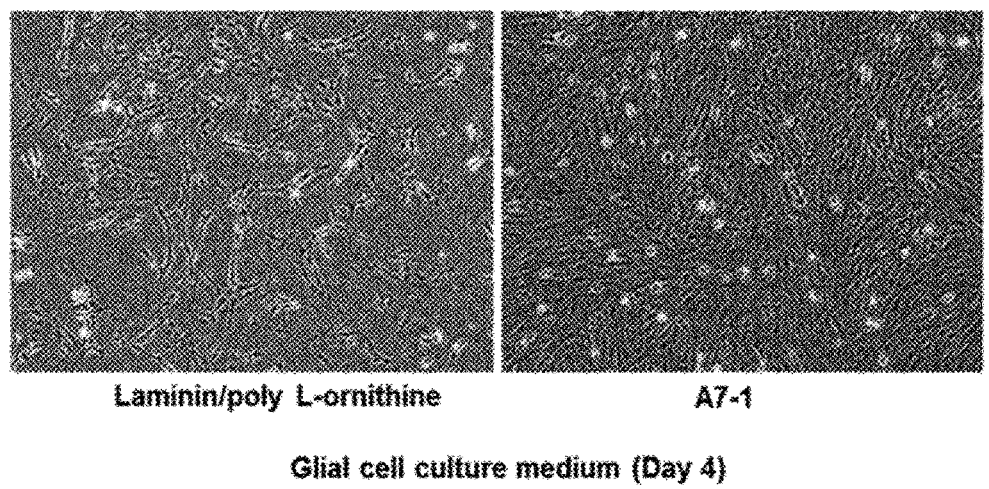
Figure 9C:
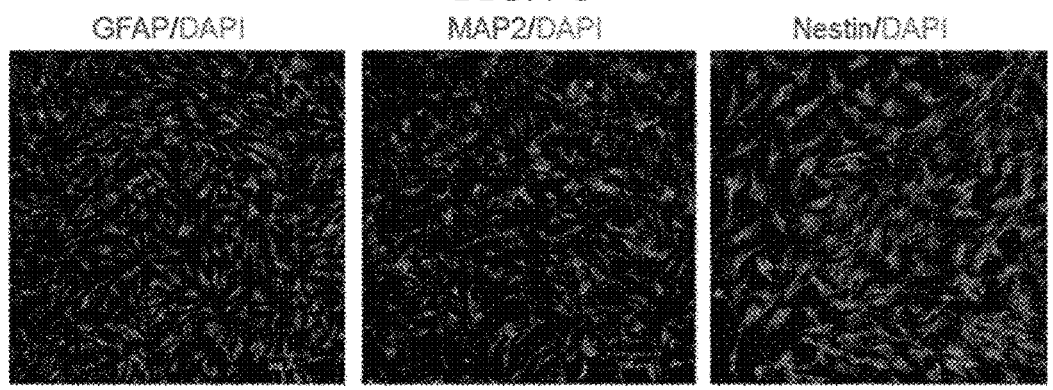

Results are shown in FIGS. 9A-9C. From FIG. 9A in which the CCK-8 was analyzed at hours indicated in the group culture in the plate treated with laminin and poly-L-ornithin or with the present peptide, it is observed that the cells treated with the present peptide A7-1 shows the results significantly different from other groups. FIG. 9B shows the results of microscopic observation at 4 days of culture, indicating that the present peptide is the best in the adhesiveness even under the condition of the same number of cells. FIG. 9C is the results to confirm that the primary nerve cells cultured in the plate coated with the present peptide are nerve cells by using the nerve cell specific marker, GFAP, MAP2 and Nestin, which were analyzed by immunofluorescent analysis and confocal microscopy. The results indicate that the present peptide has an adhesiveness superior to the currently used ones.

Example 10

Improvement of the Attachment of Human MSC (Mesenchymal Stem Cell)

Figure 10A:
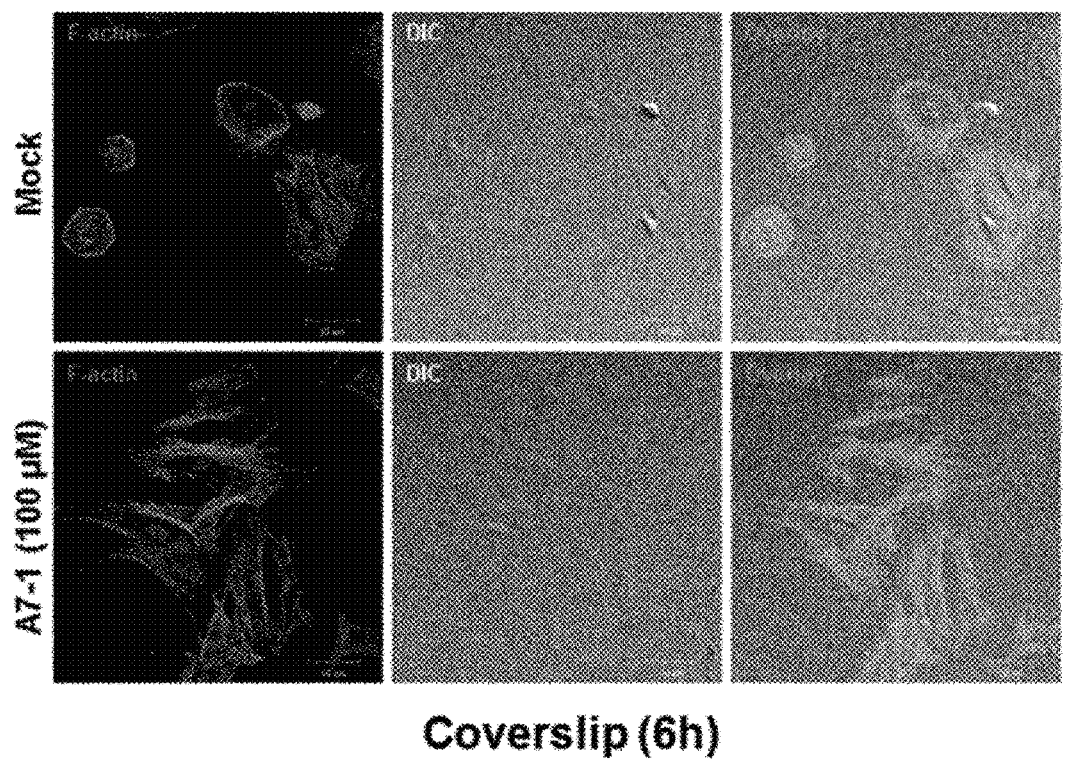
FIGS. 10A to 10C are the results showing that the adhesion progression is promoted by the present peptides, in which the cells were analyzed 6 hours after the culture.
Figure 10B:
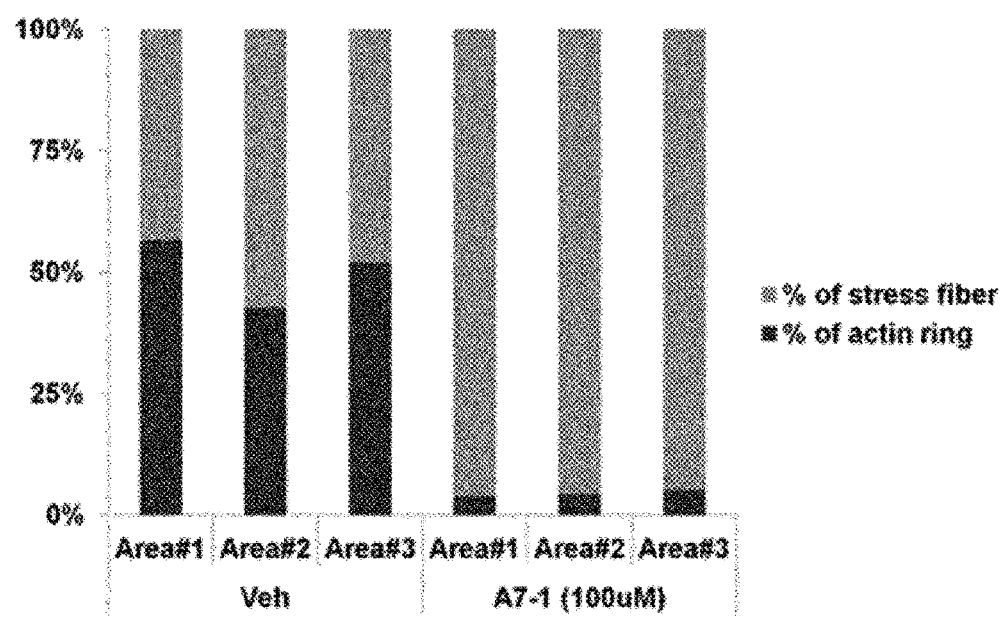
Figure 10C:
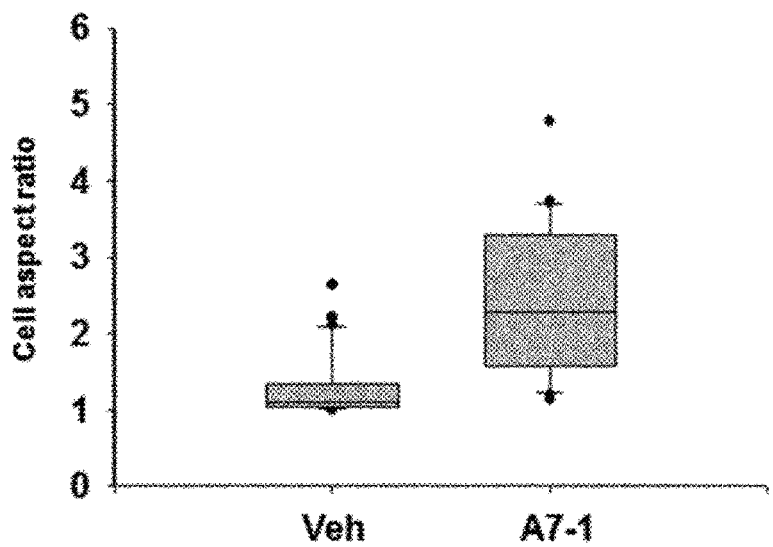

A7-1 peptide of the present disclosure was used to coat a sterilized coverslip at the concentration of 100 μM. Then MSCs (Mesenchymal Stem cell) were cultured on the coated coverslip for 6 hrs and the adhesion progression was examined by staining the cells with fluorescent dye Rhodamine Phalloidin (Life Technology Cat.# R415) for actin fibers and DAPI (Sigma D9542) for nuclei of the cells, which were detected by confocal microscope. In this case, cells cultured on the coverslips not coated with A7-1 peptide were used as a negative control. Results are shown in FIGS. 10A-10C. From FIG. 10A, it is observed that the majority of negative control cells still stay in the actin-ring formation indicative of the early stage of adhesion progression. In contrast, it is observed that the majority of cells treated with A7-1 are in the stress fiber formation stage past the actin-ring stage. FIG. 10B is a graph showing the quantification result of FIG. 10A. FIG. 10C is a graph showing geometric shape of the cell as they are attaching to the coverslip (cell aspect ratio:width/height of a cell, 1 indicates a perfect round shape and the very early stage of the adhesiveness progression. Refer to: Prager-Khoutorsky et al., 2011. Nature Cell Biology 13, 1457-1465) and indicates an excellent adhesiveness of A7-1 compared to controls.

Example 11

Test of Adhesiveness of the Present Peptides with Various Amino Acid Sequence

The peptides as listed and described in Table 1 were synthesized as described in Example 1 and tested for its adhesiveness to heparin and N-Acetylglucosamine (GAG) according to the methods described in Example 5.

TABLE 1

| Name | Amino acid sequence (N→C) | SEQ ID NO | Brief description |
| --- | --- | --- | --- |
| Mock | Mock | | PBS only |
| P#1 | RQLVVK | 15 | Peptide #1 |
| P#2 | FRALPC | 6 | Peptide #2 |
| 12-mer (B) | FRALPCRQLVVK | 16 | Peptide #2 + Peptide #1 |
| 12-mer (A)-NH2 | RQLVVKFRALPC | 17 | Carboxyl group of 12-mer (A) peptide substituted with NH$_2$ |
| 2x 12-mer (A) | RQLVVKFRALPCRQLVVKFRALPC | 18 | Two consecutive 12-mer (A) peptide |
| ΔC12 | RQLVVKFRALP | 19 | Deletion of Cys at position 12 of A peptide |

TABLE 1-continued

| Name | Amino acid sequence (N→C) | SEQ ID NO | Brief description |
|---|---|---|---|
| ΔP11C12 | RQLVVKFRAL | 20 | Deletion of Pro and Cys at positions 11 and 12 of A peptide |
| R1K | KQLVVKFRALPC | 21 | Substitution of Arg at position 1 of A peptide with Lys |
| ΔTVV | RQKFRALPC | 22 | LVV deletion from A peptide |
| LVV > EEE | RQEEEKFRALPC | 23 | Substitution of LVV of A peptide with EEE(charged or polar) |
| LVV > AAA | RQAAAKFRALPC | 24 | Substitution of LVV of A peptide with other hydrophobic residues |
| ΔAL | RQLVVKFRPC | 25 | AL deletion from A peptide |
| AL > EE | RQLVVKFREEPC | 26 | Substitution of AL of A peptide with EE (charged or polar) |
| AL > VV | RQLVVKFRVVPC | 27 | Substitution of AL of A peptide with other hydrophobic residues |
| Hpho > Hphil | RQEEEKFREEPC | 28 | Substitution of Hydrophobic residues of A peptide with hydrophilic residues |
| (+) > H | EQLVVEFEALPC | 29 | Substitution of Positive > negative charged AA substitution |
| F7Y | RQLVVKYRALPC | 30 | Substitution of Phe at position 7 of A peptide with Tyr |
| F7W | RQLVVKWRALPC | 31 | Substitution of Phe at position 7 of A peptide with Trp. |
| Q2N | RNLVVKFRALPC | 32 | Substitution of Q of A peptide with N (nonpolar substitution) |
| Q2S | RSLVVKFRALPC | 33 | Substitution of Q of A peptide with S (Polar substitution) |
| 2x(QLVV) | R-(QLVV)2-KFRALPC | 34 | QLVV addition |
| 3x(QLVV) | R-(QLVV)3-KFRALPC | 35 | QLVV addition |
| 4x(QLVV) | R-(QLVV)4-KFRALPC | 36 | QLVV addition |
| 2x(FRALP) | RQLVVK-(FRALPC)2 | 37 | FRALPC addition |
| 2xR1 | (R)2-QLVVKFRALPC | 38 | Arg addition |
| 5xR1 | (R)5-QLVVKFRALPC | 39 | Arg addition |
| 10xR1 | (R)10-QLVVKFRALPC | 40 | Arg addition |
| 15xR1 | (R)15-QLVVKFRALPC | 41 | Arg addition |

Figure 11:
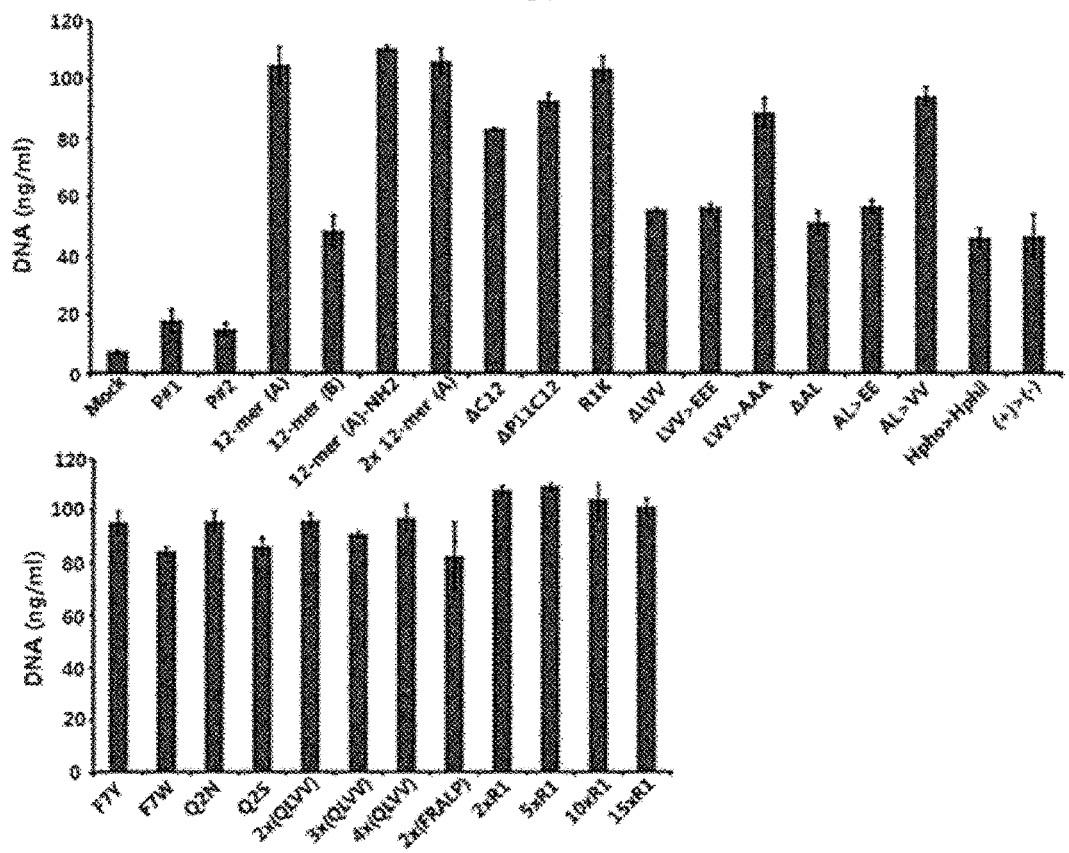
FIG. 11 is the results of testing various peptides according to the present disclosure in promoting the adhesiveness through an interaction with heparin and GAG, major components of extracellular matrix.

Results are shown in FIG. 11. From the figure, it is observed that the present peptides in various combinations of a first region (formula), a second region (formula) and a third region (formula), or the present peptides having substitutions with amino acid residues as defined in the present disclosure exhibits the adhesiveness.

Example 12

Figure 12:
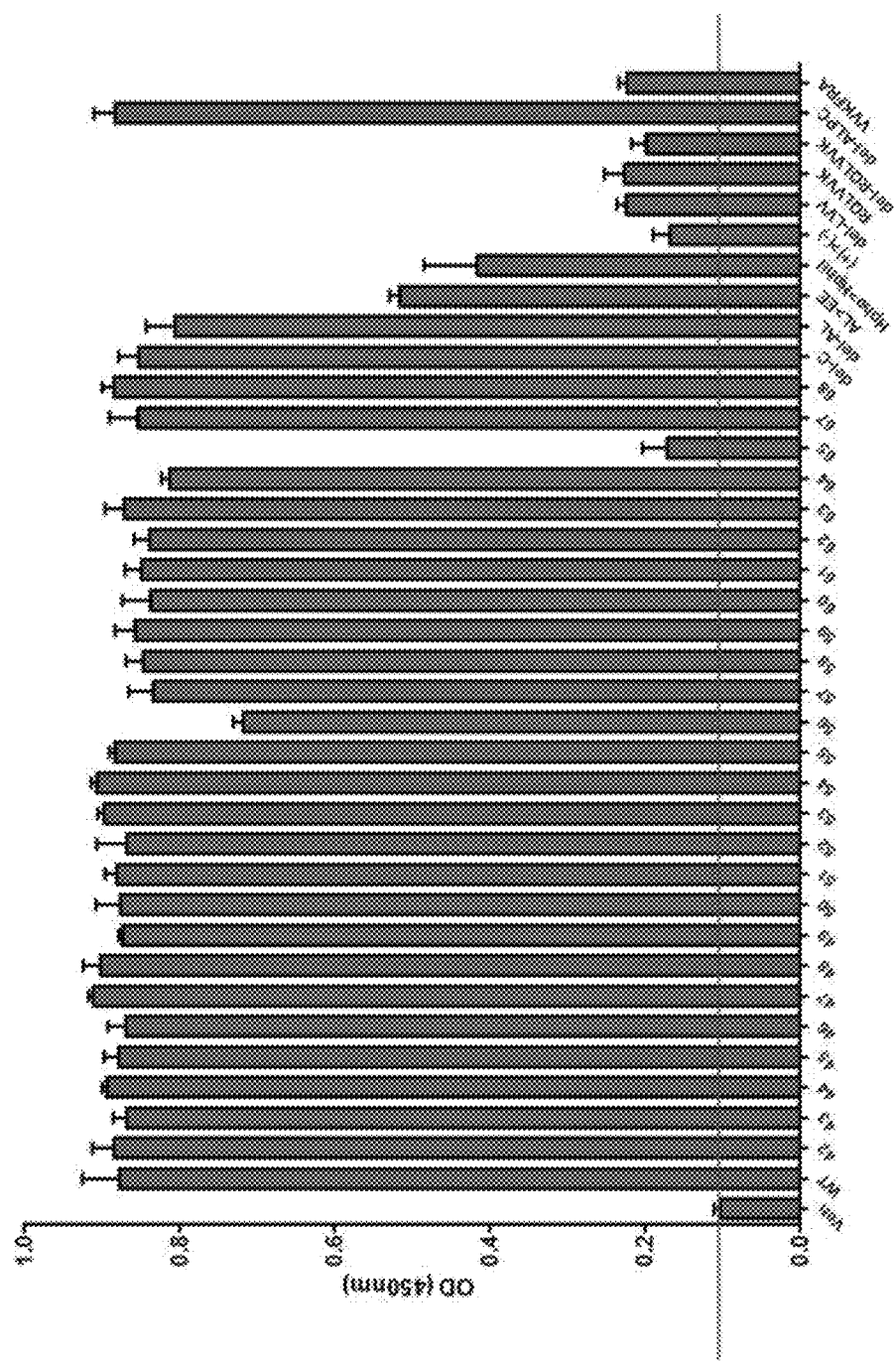
FIG. 12 is the results of testing various peptides generated based on the sequence A7-1 peptide in promoting the adhesiveness. Some of the present peptides as used in FIG. 11 were also used. The terms veh, wt and numbers on the X-axis each indicates a negative control, A7-1 peptide and sequence identification numbers, respectively.

Test II of Adhesiveness of the Present Peptides with Various Amino Acid Sequences The peptides having substitutions at various positions using RQLVVKFRALPC (SEQ ID NO: 17) as parent peptide were generated as listed in Table 2 and tested for the adhesiveness as in EXAMPLE 11, in which the substituted residues were determined in consideration of chemical characteristics, size and charges of the side chain of the substituted residues and/or the results of the peptide listed in Table 1 and indicated in bold letters. The results are shown in FIG. 12. All the peptides tested have been found to have adhesiveness improved in comparison to the negative control (Veh),

TABLE 2

| | Amino acid sequence | SEQ ID NO |
|---|---|---|
| A | RQLVVKFRALPC | 17 |
| | KQLVVKFRALPC | 21 |

TABLE 2-continued

| Amino acid sequence | SEQ ID NO |
|---|---|
| RNLVVKFRALPC | 32 |
| RSLVVKFRALPC | 33 |
| RQVVVKFRALPC | 42 |
| RQIVVKFRALPC | 43 |
| RQAVVKFRALPC | 44 |
| RQEVVKFRALPC | 45 |
| RQLLVKFRALPC | 46 |
| RQLIVKFRALPC | 47 |
| RQLAVKFRALPC | 48 |
| RQLEVKFRALPC | 49 |
| RQLVLKFRALPC | 50 |
| RQLVIKFRALPC | 51 |
| RQLVAKFRALPC | 52 |
| RQLVEKFRALPC | 53 |
| RQAAAKFRALPC | 24 |
| RQEEEKFRALPC | 23 |
| RQLVVRFRALPC | 54 |
| RQLVVKYRALPC | 30 |
| RQLVVKWRALPC | 31 |
| RQLVVKFKALPC | 55 |
| RQLVVEFEALPC | 56 |
| RQLVVKFRLLPC | 57 |
| RQLVVKFRILPC | 58 |
| RQLVVKFRVLPC | 59 |
| RQLVVKFRELPC | 60 |
| RQLVVKFRAAPC | 61 |
| RQLVVKFRAIPC | 62 |
| RQLVVKFRAVPC | 63 |
| RQLVVKFRAEPC | 64 |
| RQLVVKFRVVPC | 27 |
| RQLVVKFREEPC | 26 |
| RQEEEKFREEPC | 28 |
| RQEEEEFEEEPC | 65 |
| RQLVVKFRALXC | 66 |
| RQLVVKFRALPS | 67 |
| RQLVVKFRALPT | 68 |
| RQLVVKFRALPX | 69 |

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention. The contents of all publications disclosed as references herein are incorporated herein by reference.

What is claimed is:

1. An isolated bio-adhesive polypeptide:
   (i) consisting of the amino acid sequence as set forth in SEQ ID NOs: 15-22, 24-27, 29-37, 42-64, 67 or 68;
   (ii) consisting of the amino acid sequence as set forth in SEQ ID NOs: 15-20, 22, 24-27, 30-37, 42-64, 67 or 68 with the first amino acid of the sequence being substituted with a lysine residue;
   (iii) consisting of the amino acid sequence as set forth in SEQ ID NOs: 15-22, 24-27, 30-37, 42-64, 67 or 68 with the first amino acid of the sequence being substituted with an aspartic acid or a glutamic acid residue;
   (iv) consisting of the amino acid sequence as set forth in SEQ ID NOs: 15-20, 22, 24-27, 30-37, 42-64, 67 or 68, and 1 to 14 arginine residues at the N-terminus of the amino acid sequence;
   (v) consisting of the amino acid sequence as set forth in SEQ ID NOs: 15-22, 24-27, 29-37, 42-64, 67 or 68 with the N- or C-terminus of the sequence being substituted with an inert group,
   (vi) consisting of the amino acid sequence as set forth in SEQ ID NO: 29 with the first amino acid of the sequence being substituted with an aspartic acid, a lysine, or an arginine residue;
   (vii) consisting of the amino acid sequence as set forth in SEQ ID NO: 29 and 1 to 14 glutamic acid residues at the N-terminus of the amino acid sequence; or
   (viii) consisting of the amino acid sequence as set forth in SEQ ID NO: 21 and 1 to 14 lysine residues at the N-terminus of the amino acid sequence.

2. A composition comprising the polypeptide of claim 1.

3. A nucleic acid molecule encoding the polypeptide of claim 1.

4. A vector comprising the nucleic acid molecule of claim 3.

5. A cell comprising the vector of claim 4.

* * * * *

SEQUENCE LISTING

```
<160> NUMBER OF SEQ ID NOS: 69

<210> SEQ ID NO 1
<211> LENGTH: 5
<212> TYPE: PRT
<213> ORGANISM: Artificial Sequence
<220> FEATURE:
<223> OTHER INFORMATION: synthetic peptide

<400> SEQUENCE: 1

Gln Leu Val Val Lys
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Gln Glu Glu Glu Lys
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Gln Ala Ala Ala Lys
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Asn Leu Val Val Lys
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

Ser Leu Val Val Lys
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic peptide

<400> SEQUENCE: 6

Phe Arg Ala Leu Pro Cys
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic peptide

<400> SEQUENCE: 7

Phe Arg Glu Glu Pro Cys
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide

<400> SEQUENCE: 8

Phe Arg Val Val Pro Cys
1               5
```

```
<210> SEQ ID NO 9
<211> LENGTH: 6
<212> TYPE: PRT
<213> ORGANISM: Artificial Sequence
<220> FEATURE:
<223> OTHER INFORMATION: synthetic peptide

<400> SEQUENCE: 9

Phe Glu Ala Leu Pro Cys
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide

<400> SEQUENCE: 10

Tyr Arg Ala Leu Pro Cys
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide

<400> SEQUENCE: 11

Trp Arg Ala Leu Pro Cys
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Phe Arg Ala Leu Pro
1               5

<210> SEQ ID NO 13
<211> LENGTH: 4
<212> TYPE: PRT
<213> ORGANISM: Artificial Sequence
<220> FEATURE:
<223> OTHER INFORMATION: synthetic peptide

<400> SEQUENCE: 13

Phe Arg Ala Leu
1

<210> SEQ ID NO 14
<211> LENGTH: 4
<212> TYPE: PRT
<213> ORGANISM: Artificial Sequence
<220> FEATURE:
<223> OTHER INFORMATION: synthetic peptide

<400> SEQUENCE: 14

Phe Arg Pro Cys
1
```

```
<210> SEQ ID NO 15
<211> LENGTH: 6
<212> TYPE: PRT
<213> ORGANISM: Artificial Sequence
<220> FEATURE:
<223> OTHER INFORMATION: synthetic peptide

<400> SEQUENCE: 15

Arg Gln Leu Val Val Lys
1               5

<210> SEQ ID NO 16
<211> LENGTH: 12
<212> TYPE: PRT
<213> ORGANISM: Artificial Sequence
<220> FEATURE:
<223> OTHER INFORMATION: synthetic peptide

<400> SEQUENCE: 16

Phe Arg Ala Leu Pro Cys Arg Gln Leu Val Val Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: synthetic peptide

<400> SEQUENCE: 17

Arg Gln Leu Val Val Lys Phe Arg Ala Leu Pro Cys
1               5                   10

<210> SEQ ID NO 18
<211> LENGTH: 24
<212> TYPE: PRT
<213> ORGANISM: Artificial Sequence
<220> FEATURE:
<223> OTHER INFORMATION: synthetic peptide

<400> SEQUENCE: 18

Arg Gln Leu Val Val Lys Phe Arg Ala Leu Pro Cys Arg Gln Leu Val
1               5                   10                  15

Val Lys Phe Arg Ala Leu Pro Cys
            20

<210> SEQ ID NO 19
<211> LENGTH: 11
<212> TYPE: PRT
<213> ORGANISM: Artificial Sequence
<220> FEATURE:
<223> OTHER INFORMATION: synthetic peptide

<400> SEQUENCE: 19

Arg Gln Leu Val Val Lys Phe Arg Ala Leu Pro
1               5                   10

<210> SEQ ID NO 20
<211> LENGTH: 10
<212> TYPE: PRT
<213> ORGANISM: Artificial Sequence
<220> FEATURE:
<223> OTHER INFORMATION: synthetic peptide

<400> SEQUENCE: 20

Arg Gln Leu Val Val Lys Phe Arg Ala Leu
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: synthetic peptide

<400> SEQUENCE: 21

Lys Gln Leu Val Val Lys Phe Arg Ala Leu Pro Cys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

<400> SEQUENCE: 22

Arg Gln Lys Phe Arg Ala Leu Pro Cys
1               5

<210> SEQ ID NO 23
<211> LENGTH: 12
<212> TYPE: PRT
<213> ORGANISM: Artificial Sequence
<220> FEATURE:
<223> OTHER INFORMATION: synthetic peptide

<400> SEQUENCE: 23

Arg Gln Glu Glu Glu Lys Phe Arg Ala Leu Pro Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: synthetic peptide

<400> SEQUENCE: 24

Arg Gln Ala Ala Ala Lys Phe Arg Ala Leu Pro Cys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic peptide

<400> SEQUENCE: 25

Arg Gln Leu Val Val Lys Phe Arg Pro Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic peptide

<400> SEQUENCE: 26

Arg Gln Leu Val Val Lys Phe Arg Glu Glu Pro Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic peptide

<400> SEQUENCE: 27

Arg Gln Leu Val Val Lys Phe Arg Val Val Pro Cys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide

<400> SEQUENCE: 28

Arg Gln Glu Glu Glu Lys Phe Arg Glu Glu Pro Cys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: synthetic peptide

<400> SEQUENCE: 29

Glu Gln Leu Val Val Glu Phe Glu Ala Leu Pro Cys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: synthetic peptide

<400> SEQUENCE: 30

Arg Gln Leu Val Val Lys Tyr Arg Ala Leu Pro Cys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: synthetic peptide

<400> SEQUENCE: 31

Arg Gln Leu Val Val Lys Trp Arg Ala Leu Pro Cys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthetic peptide

<400> SEQUENCE: 32

Arg Asn Leu Val Val Lys Phe Arg Ala Leu Pro Cys
1               5                   10

```
<210> SEQ ID NO 33
<211> LENGTH: 12
<212> TYPE: PRT
<213> ORGANISM: Artificial Sequence
<220> FEATURE:
<223> OTHER INFORMATION: synthetic peptide

<400> SEQUENCE: 33

Arg Ser Leu Val Val Lys Phe Arg Ala Leu Pro Cys
1               5                   10

<210> SEQ ID NO 34
<211> LENGTH: 16
<212> TYPE: PRT
<213> ORGANISM: Artificial Sequence
<220> FEATURE:
<223> OTHER INFORMATION: synthetic peptide

<400> SEQUENCE: 34

Arg Gln Leu Val Val Gln Leu Val Val Lys Phe Arg Ala Leu Pro Cys
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: synthetic peptide

<400> SEQUENCE: 35

Arg Gln Leu Val Val Gln Leu Val Val Gln Leu Val Val Lys Phe Arg
1               5                   10                  15

Ala Leu Pro Cys
            20

<210> SEQ ID NO 36
<211> LENGTH: 24
<212> TYPE: PRT
<213> ORGANISM: Artificial Sequence
<220> FEATURE:
<223> OTHER INFORMATION: synthetic peptide

<400> SEQUENCE: 36

Arg Gln Leu Val Val Gln Leu Val Val Gln Leu Val Val Gln Leu Val
1               5                   10                  15

Val Lys Phe Arg Ala Leu Pro Cys
            20

<210> SEQ ID NO 37
<211> LENGTH: 18
<212> TYPE: PRT
<213> ORGANISM: Artificial Sequence
<220> FEATURE:
<223> OTHER INFORMATION: synthetic peptide

<400> SEQUENCE: 37

Arg Gln Leu Val Val Lys Phe Arg Ala Leu Pro Cys Phe Arg Ala Leu
1               5                   10                  15

Pro Cys

<210> SEQ ID NO 38
<211> LENGTH: 13
<212> TYPE: PRT
<213> ORGANISM: Artificial Sequence
<220> FEATURE:
<223> OTHER INFORMATION: synthetic peptide
```

<400> SEQUENCE: 38

Arg Arg Gln Leu Val Val Lys Phe Arg Ala Leu Pro Cys
1               5                   10

<210> SEQ ID NO 39
<211> LENGTH: 16
<212> TYPE: PRT
<213> ORGANISM: Artificial Sequence
<220> FEATURE:
<223> OTHER INFORMATION: synthetic peptide

<400> SEQUENCE: 39

Arg Arg Arg Arg Arg Gln Leu Val Val Lys Phe Arg Ala Leu Pro Cys
1               5                   10                  15

<210> SEQ ID NO 40
<211> LENGTH: 21
<212> TYPE: PRT
<213> ORGANISM: Artificial Sequence
<220> FEATURE:
<223> OTHER INFORMATION: synthetic peptide

<400> SEQUENCE: 40

Arg Arg Arg Arg Arg Arg Arg Arg Arg Arg Gln Leu Val Val Lys Phe
1               5                   10                  15

Arg Ala Leu Pro Cys
            20

<210> SEQ ID NO 41
<211> LENGTH: 26
<212> TYPE: PRT
<213> ORGANISM: Artificial Sequence
<220> FEATURE:
<223> OTHER INFORMATION: synthetic peptide

<400> SEQUENCE: 41

Arg Arg Arg Arg Arg Arg Arg Arg Arg Arg Arg Arg Arg Arg Arg Gln
1               5                   10                  15

Leu Val Val Lys Phe Arg Ala Leu Pro Cys
            20                  25

<210> SEQ ID NO 42
<211> LENGTH: 12
<212> TYPE: PRT
<213> ORGANISM: Artificial Sequence
<220> FEATURE:
<223> OTHER INFORMATION: synthetic peptide

<400> SEQUENCE: 42

Arg Gln Val Val Val Lys Phe Arg Ala Leu Pro Cys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: synthetic peptide

<400> SEQUENCE: 43

Arg Gln Ile Val Val Lys Phe Arg Ala Leu Pro Cys
1               5                   10

<210> SEQ ID NO 44

```
<211> LENGTH: 12
<212> TYPE: PRT
<213> ORGANISM: Artificial Sequence
<220> FEATURE:
<223> OTHER INFORMATION: synthetic peptide

<400> SEQUENCE: 44

Arg Gln Ala Val Val Lys Phe Arg Ala Leu Pro Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: synthetic peptide

<400> SEQUENCE: 45

Arg Gln Glu Val Val Lys Phe Arg Ala Leu Pro Cys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: synthetic peptide

<400> SEQUENCE: 46

Arg Gln Leu Leu Val Lys Phe Arg Ala Leu Pro Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: synthetic peptide

<400> SEQUENCE: 47

Arg Gln Leu Ile Val Lys Phe Arg Ala Leu Pro Cys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: synthetic peptide

<400> SEQUENCE: 48

Arg Gln Leu Ala Val Lys Phe Arg Ala Leu Pro Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: synthetic peptide

<400> SEQUENCE: 49

Arg Gln Leu Glu Val Lys Phe Arg Ala Leu Pro Cys
1               5                   10

<210> SEQ ID NO 50
<211> LENGTH: 12
```

```
<212> TYPE: PRT
<213> ORGANISM: Artificial Sequence
<220> FEATURE:
<223> OTHER INFORMATION: synthetic peptide

<400> SEQUENCE: 50

Arg Gln Leu Val Leu Lys Phe Arg Ala Leu Pro Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: synthetic peptide

<400> SEQUENCE: 51

Arg Gln Leu Val Ile Lys Phe Arg Ala Leu Pro Cys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: synthetic peptide

<400> SEQUENCE: 52

Arg Gln Leu Val Ala Lys Phe Arg Ala Leu Pro Cys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: synthetic peptide

<400> SEQUENCE: 53

Arg Gln Leu Val Glu Lys Phe Arg Ala Leu Pro Cys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: synthetic peptide

<400> SEQUENCE: 54

Arg Gln Leu Val Val Arg Phe Arg Ala Leu Pro Cys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: synthetic peptide

<400> SEQUENCE: 55

Arg Gln Leu Val Val Lys Phe Lys Ala Leu Pro Cys
1               5                   10

<210> SEQ ID NO 56
<211> LENGTH: 12
<212> TYPE: PRT
```

```
<213> ORGANISM: Artificial Sequence
<220> FEATURE:
<223> OTHER INFORMATION: synthetic peptide

<400> SEQUENCE: 56

Arg Gln Leu Val Val Glu Phe Glu Ala Leu Pro Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: synthetic peptide

<400> SEQUENCE: 57

Arg Gln Leu Val Val Lys Phe Arg Leu Leu Pro Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: synthetic peptide

<400> SEQUENCE: 58

Arg Gln Leu Val Val Lys Phe Arg Ile Leu Pro Cys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: synthetic peptide

<400> SEQUENCE: 59

Arg Gln Leu Val Val Lys Phe Arg Val Leu Pro Cys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: synthetic peptide

<400> SEQUENCE: 60

Arg Gln Leu Val Val Lys Phe Arg Glu Leu Pro Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: synthetic peptide

<400> SEQUENCE: 61

Arg Gln Leu Val Val Lys Phe Arg Ala Ala Pro Cys
1               5                   10

<210> SEQ ID NO 62
<211> LENGTH: 12
<212> TYPE: PRT
<213> ORGANISM: Artificial Sequence
```

```
<220> FEATURE:
<223> OTHER INFORMATION: synthetic peptide

<400> SEQUENCE: 62

Arg Gln Leu Val Val Lys Phe Arg Ala Ile Pro Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: synthetic peptide

<400> SEQUENCE: 63

Arg Gln Leu Val Val Lys Phe Arg Ala Val Pro Cys
1               5                   10

<210> SEQ ID NO 64
<211> LENGTH: 12
<212> TYPE: PRT
<213> ORGANISM: Artificial Sequence
<220> FEATURE:
<223> OTHER INFORMATION: synthetic peptide

<400> SEQUENCE: 64

Arg Gln Leu Val Val Lys Phe Arg Ala Glu Pro Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: synthetic peptide

<400> SEQUENCE: 65

Arg Gln Glu Glu Glu Glu Phe Glu Glu Glu Pro Cys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (11)
<223> OTHER INFORMATION: any amino acids

<400> SEQUENCE: 66

Arg Gln Leu Val Val Lys Phe Arg Ala Leu Xaa Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: synthetic peptide

<400> SEQUENCE: 67

Arg Gln Leu Val Val Lys Phe Arg Ala Leu Pro Ser
1               5                   10

<210> SEQ ID NO 68
```

```
<211> LENGTH: 12
<212> TYPE: PRT
<213> ORGANISM: Artificial Sequence
<220> FEATURE:
<223> OTHER INFORMATION: synthetic peptide

<400> SEQUENCE: 68

Arg Gln Leu Val Val Lys Phe Arg Ala Leu Pro Thr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (12)
<223> OTHER INFORMATION: any amino acids

<400> SEQUENCE: 69

Arg Gln Leu Val Val Lys Phe Arg Ala Leu Pro Xaa
1               5                   10
```